(12) United States Patent
Plumbley et al.

(10) Patent No.: US 12,094,578 B2
(45) Date of Patent: Sep. 17, 2024

(54) SHORTLIST SELECTION MODEL FOR ACTIVE LEARNING

(71) Applicant: BENEVOLENTAI TECHNOLOGY LIMITED, London (GB)

(72) Inventors: Dean Plumbley, London (GB); Marwin Hans Siegfried Segler, Southsea (GB)

(73) Assignee: BenevolentAI Technology Limited, London (GB)

( * ) Notice: Subject to any disclaimer, the term of this patent is extended or adjusted under 35 U.S.C. 154(b) by 801 days.

(21) Appl. No.: 17/041,622

(22) PCT Filed: Mar. 29, 2019

(86) PCT No.: PCT/GB2019/050924
§ 371 (c)(1),
(2) Date: Sep. 25, 2020

(87) PCT Pub. No.: WO2019/186195
PCT Pub. Date: Oct. 3, 2019

(65) Prior Publication Data
US 2021/0012862 A1    Jan. 14, 2021

(30) Foreign Application Priority Data

Mar. 29, 2018    (GB) ...................................... 1805296

(51) Int. Cl.
*G06F 11/30*    (2006.01)
*G06F 18/214*    (2023.01)
(Continued)

(52) U.S. Cl.
CPC ......... *G16C 20/70* (2019.02); *G06F 18/2155* (2023.01); *G06N 20/00* (2019.01); *G16C 20/10* (2019.02)

(58) Field of Classification Search
CPC ...................................................... G16C 20/70
See application file for complete search history.

(56) References Cited

U.S. PATENT DOCUMENTS

2005/0278124 A1    12/2005  Duffy et al.
2012/0191631 A1     7/2012  Breckenridge et al.

FOREIGN PATENT DOCUMENTS

WO    2012/112534 A2    8/2012

OTHER PUBLICATIONS

Ramprasad et el., "Machine Learning in materials informatics: recent applications and prospects", NPJ Computational Material, vol. 3, No. 54, dated Dec. 1, 2017, 13 pgs (Year: 2017).*

(Continued)

*Primary Examiner* — Phuong Huynh
(74) *Attorney, Agent, or Firm* — Smith Baluch LLP

(57) ABSTRACT

Method(s) and apparatus are provided for generating a selection model based on a machine learning (ML) technique, the selection model for selecting a shortlist of compounds requiring validation with a particular property. An iterative procedure or feedback loop for generating the selection model may include: receiving a prediction result list output from a property model for predicting whether a plurality of compounds are associated with a particular property and an property model score; retraining the selection model based on the property model score and/or the prediction result list; selecting a shortlist of compounds using the retrained selection model from the plurality of compounds associated with the prediction result list; sending the selected shortlist of compounds for validation with the particular property, where another ML technique is used to update the property model based on the validation; repeating the receiving and retraining of the selection model until determining the selection model has been validly trained.

30 Claims, 7 Drawing Sheets

(51) Int. Cl.
 *G06N 20/00* (2019.01)
 *G16C 20/10* (2019.01)
 *G16C 20/70* (2019.01)

(56) References Cited

OTHER PUBLICATIONS

PCT Written Opinion and Search Report issued in related PCT Patent Application No. PCT/GB2019/050924 dated Nov. 12, 2019.
Ramprasad, R., et al., "Machine Learning in Materials Informatics: recent applications and prospects", NPJ Computational Materials, vol. 3, No. 54, dated Dec. 1, 2017, 13 pgs.
Gramatica, P., et al., "Classification of Organic Solvents and Modelling of their Physico-chemical Properties by Chemometric Methods using Different Sets of Molecular Descriptors", Trac Trends in Analytical Chemistry, Elsevier, Amsterdam, vol. 18, No. 7, dated Jul. 1, 1999, 11 pgs.
Non-Final Office Action in U.S. Appl. No. 17/041,620 dated Feb. 1, 2024, 32 pages.
Pending claims in U.S. Appl. No. 17/041,620 dated Feb. 1, 2024, 8 pages.
Popova, et al., "Deep reinforcement learning for de novo drug design." Science advances 4.7 (2018): eaap7885, 24 pages.
Popova, M., et al., "Deep Reinforcement Learning for De-Novo Design", ARXIV.ORG, Cornell University Library, 201 OLIN Library Cornell University, NY, dated Nov. 29, 2017, 28 pgs.

\* cited by examiner $\{R_I\}=$

| Compound $C_I$ | Score $P_I$ |
|---|---|
| $C_1$ | $P_1 = P_{CP} = 100\%$ |
| $C_2$ | $P_2 = P_{CP} = 100\%$ |
| ⋮ | ⋮ |
| $C_I$ | $P_I = X_i$ $P_{CN} < X_i < P_{CP}$ |
| ⋮ | ⋮ |
| $C_{N-1}$ | $P_{L-1} = P_{CN} = 0\%$ |
| $C_N$ | $P_L = P_{CN} = 0\%$ |

*FIG. 2*

SHORTLIST SELECTION MODEL FOR ACTIVE LEARNING

CROSS-REFERENCE TO RELATED PATENT APPLICATIONS

This patent application is the 35 U.S.C. 371 national stage of International Patent Application PCT/GB2019/050924 filed 29 Mar. 2019; which claims the benefit of priority to GB Application 1805296.9 filed 29 Mar. 2018, which is incorporated by reference herein for all purposes.

The present application relates to apparatus, system(s) and method(s) for selecting a shortlist of compounds for active learning and model validation.

BACKGROUND

Informatics is the application of computer and informational techniques and resources for interpreting data in one or more academic and/or scientific fields. Cheminformatics' and bioinformatics includes the application of computer and informational techniques and resources for interpreting chemical and/or biological data. This may include solving and/or modelling processes and/or problems in the field(s) of chemistry and/or biology. For example, these computing and information techniques and resources may transform data into information, and subsequently information into knowledge for rapidly creating compounds and/or making improved decisions in, by way of example only but not limited to, the field of drug identification, discovery and optimization.

Machine learning techniques are computational methods that can be used to devise complex analytical models and algorithms that lend themselves to solving complex problems such as creation and prediction of whether compounds have one or more characteristics and/or property(ies). Although, there are a myriad of ML techniques that may be used or selected for predicting whether compounds have a particular property or characteristic, there is typically a shortage of training data for suitably training a ML technique to generate suitable a trained ML model for predicting whether a compound has a particular property, which is referred to herein as a property model. If an ML technique is used to generate a property model based on insufficient labelled training data then the resulting property model may not be able to reliably predict whether a compound has a particular property for a broad range of compounds.

Generating a labelled training dataset for use in training an ML technique to generate accurate and reliable property models for predicting whether a compound has a particular property is costly, time consuming and error prone due to human error. The complexity of this task exponentially increases as the number of properties/characteristics that need to be predicted increases with each of a number of property models being used to predict whether a compound has one or more of the plurality of properties and/or characteristics. There is a desire to improve the generation of labelled training datasets and select only those compounds with unknown associations to a particular property for maximising the quality of the property model whilst minimising the number of compounds selected. This would further improve training ML techniques for generating accurate and reliable property models for predicting whether compounds have one or more particular property(ies) and allow researchers, data scientists, engineers, and analysts to make rapid improvements in the field of drug identification, discovery and optimisation.

The embodiments described below are not limited to implementations which solve any or all of the disadvantages of the known approaches described above.

SUMMARY

This Summary is provided to introduce a selection of concepts in a simplified form that are further described below in the Detailed Description. This Summary is not intended to identify key features or essential features of the claimed subject matter, nor is it intended to be used to determine the scope of the claimed subject matter; variants and alternative features which facilitate the working of the invention and/or serve to achieve a substantially similar technical effect should be considered as falling into the scope of the invention disclosed herein.

The present disclosure provides methods and apparatus for a selection model that predicts the best selection of a shortlist of compounds from a prediction result list output by a machine learning (ML) model for predicting whether a compound exhibits or has a particular property (e.g. a property model). The ML model is generated by training a ML technique based on a labelled training dataset associated with compounds exhibiting/associated with a particular property. The selection model may be generated based on an iterative and semi-automated/automated approach for training another ML technique such as, by way of example only but not limited to, a reinforcement learning (RL) technique to select the best shortlist of compounds from the prediction result list. The RL technique is trained to generate a selection model that predicts the best selection of a shortlist of compounds for validation from the prediction result list of the ML model (e.g. property model), where validation results from the shortlist of compounds can be used to enhance the ML model. The validation of the selected shortlist may include validating the association of each of the compounds in the selected shortlist with the particular property. The validation results may include an indication of each compounds association with the particular property; these may be used to generate further labelled training datasets for updating or enhancing the ML model. Thus, the selection model assists in enhancing the training of ML techniques for generating accurate and reliable property models.

The selection model that is generated may be applicable when there is insufficient labelled training data for training the ML technique to generate a sufficiently accurate property model for predicting whether a compound has a particular property. The selection model is configured to enhance the labelled training dataset by selecting the best subset of compounds that should be validated in relation to the particular property that would, when validated, result in updating the property model and maximise or at least improve its predictive performance. For example, validation results for the selected shortlist of compounds may be used to generate further labelled training datasets, which can be used in retraining the ML technique to generate an updated property model that maximises or at least improves the property model's predictive performance.

The RL technique may also be trained to generate a selection model, and/or validation model, for also predicting which validation method may be selected for validating the selected shortlist of compounds. For example, the selection model (validation model) may be further configured to predict whether and/or when to select a validation method based on computer analysis/simulation or a validation method based on laboratory experimentation to validate the selected shortlist of compounds against the particular property. This may further minimise the costs in, by way of example but not limited to, time, computing resources, and/or expenses and the like associated with validating the shortlist of compounds.

In a first aspect, the present disclosure provides a computer-implemented method for generating a selection model based on a ML technique, the selection model for selecting a shortlist of compounds requiring validation with a particular property. The method may use an iterative procedure/feedback loop that may be performed for generating the selection model until it is considered to be validly trained. The procedure for each iteration of the feedback loop may include, by way of example only but is not limited to: receiving a prediction result list output from a property model for predicting whether a plurality of compounds are associated with a particular property and an property model score; training/retraining or updating the selection model based on the property model score and/or the prediction result list; selecting a shortlist of compounds using the retrained selection model from the plurality of compounds associated with the prediction result list; sending the selected shortlist of compounds for validation with the particular property, wherein another ML technique is used to update the property model based on the validation; repeating at least the receiving and retraining of the selection model until determining the selection model has been validly trained. The procedure/loop may be repeated using the updated selection model until it is determined the selection model has been validly trained.

Preferably, the selection model may be generated by training an ML technique based on the property model score. As an option, the selection model may be generated by training an ML technique associated with reinforcement learning (e.g. an RL technique) based on the property model score and/or prediction result list. Preferably, the ML technique for generating and/or updating the property model is trained or updates based on a labelled training dataset comprising data representative of a subset or set of a plurality of compounds and their known association with the particular property.

Preferably, retraining the selection model further comprises determining whether to retrain the selection model for selecting a shortlist of compounds based on the property model score and previous property model score(s).

Preferably, the method further comprises: selecting, using the selection model, a set of compounds for the shortlist of compounds from the prediction result list for validation; validating the association of each of the compounds in the selected shortlist of compounds with the particular property; and sending the validation shortlist of compounds to the ML technique for updating the property model based on the ML technique and the validated shortlist of compounds. For example, the validation shortlist of compounds may be sent to the ML technique used for generating the property model based on the validated shortlist of compounds; retraining the ML technique based on the validated shortlist of compounds as well as the labelled training dataset may be used to update the property model.

Preferably, the ML technique uses a labelled training dataset for generating the property model, the labelled training dataset being associated with a subset of the plurality of compounds in relation to the particular property, and wherein the validation or validated shortlist of compounds (e.g. validation results in relation to the shortlist of compounds) are incorporated into the labelled training dataset for updating the property model by the ML technique that generates the property model.

Preferably, validating the selected shortlist of compounds further comprises validating the association that each compound from the shortlist of compounds has with the particular property based on either laboratory experimentation or computer analysis.

Preferably, the laboratory experimentation outputs a set of laboratory experimental validation results in relation to the selected shortlist of compounds and the property, wherein the property model is updated based on the laboratory experimentation validation results and an ML technique for generating the property model. Preferably, the computer analysis outputs a set of computer analysis validation results in relation to the selected shortlist of compounds and the particular property, wherein the property model is updated based on the computer analysis validation results and the ML technique for generating the property model.

Preferably, the selection model is further trained to select a validation method for validating the selected shortlist of compounds, wherein selecting the validation method for validating the selected shortlist of compounds further comprises: selecting whether to perform laboratory experimentation or to perform computer analysis based on the particular property and the selected shortlist of compounds; in response to selecting to perform laboratory experimentation, wherein the laboratory experimentation outputs laboratory experimentation validation results for estimating the association each compound on the selected shortlist of compounds has with the particular property, wherein the laboratory experimental validation results are used by the ML technique that generates the property model to update the property model; in response to determining to perform computer analysis, wherein the computer analysis outputs computer analysis validation results for estimating the association each compound on the selected shortlist of compounds has with the particular property, wherein the computer analysis validation results are used by the ML technique that generates the property model for updating the property model.

Preferably, the method further comprising: receiving a prediction result list output from the property model for predicting whether a plurality of compounds are associated with a particular property and an property model score; determining whether to retrain the selection model for selecting a shortlist of compounds and a validation method based on the property model score and previous property model score(s); and retraining the selection model based on the property model score and/or the prediction result list.

Preferably, when the validation method to perform laboratory experimentation is selected and the number of iterations for retraining or updating the selection model is below a predetermined threshold, the method further comprising: penalising the selection model during retraining; and selecting the validation method to perform computer analysis.

Preferably, when the validation method to perform laboratory experimentation is selected and it is determined that the validation method to perform computer analysis would further improve the property model score, the method further comprising: penalising the selection model during retraining; and selecting the validation method to perform computer analysis.

Preferably, when the validation method to perform laboratory experimentation is selected and the selected shortlist of compounds has substantially changed from a previously selected shortlist of compounds, the method further comprising: penalising the selection model during retraining; and selecting the validation method to perform computer analysis.

Preferably, when the validation method to perform computer analysis is selected and it is determined that computer analysis will yield an improvement in an property model score for the property model based on previous property model scores calculated from corresponding prediction result lists generated after each shortlist of compounds has been validated, the method further comprising: rewarding the selection model during retraining; and selecting the validation method to perform computer analysis.

Preferably, the prediction result list comprises a prediction property score indicating the association aid each compound has with the particular property.

Preferably, the prediction property score comprises a certainty score, wherein compounds that are known to have the particular property are given a positive certainty score, compounds that are known not to have the particular property are given a negative certainty score, and other compounds are given an uncertainty score between the positive certainty score and negative certainty score.

Preferably, the certainty score is a percentage certainty score, wherein the positive certainty score is 100%, the negative certainty score is 0%, and the uncertainty score is between the positive and negative certainty scores.

Preferably, retraining the selection model further comprises: indicating to the ML technique associated with the property model to revert the property model to a previous property model when the property model score does not reach a property model performance threshold compared with the corresponding previous property model score; indicating to the ML technique to retain the updated property model over a previous property model when the property model score is indicative of meeting or exceeding the property model performance threshold compared with the corresponding previous property model score; and retraining the selection model to select a set of compounds from the corresponding prediction result list based on the property model score; and repeating the steps of the first aspect, modifications thereof or as described herein until the selection model is determined to be trained.

Preferably, determining the selection model is trained further comprises: comparing the retained property model score with previous retained property model score(s); and determining the selection model has been validly trained based on a plateau of property model scores.

Preferably, the ML technique for generating and/or updating the selection model comprises at least one ML technique or combination of ML technique(s) from the group of: a recurrent neural network; convolutional neural network; reinforcement learning algorithm; and any neural network structure.

Preferably, the particular property includes a property or characteristic indicative of: a compound docking with another compound to form a stable complex; a ligand docking with a target protein, wherein the compound is the ligand; a compound docking or binding with one or more target proteins; a compound having a particular solubility or range of solubility's; a compound having a particular toxicity; any other property or characteristic associated with a compound that can be simulated based on computer simulation(s) and physical movements of atoms and molecules; any other property or characteristic associated with a compound that can be determined from an expert knowledgebase; and any other property or characteristic associated with a compound that can be determined from an experimentation. The particular property may further include a property, characteristic and/or trait indicative of: partial coefficient (e.g. Log P), distribution coefficient (e.g. Log D), solubility, toxicity, drug-target interaction, drug-drug interaction, off-target drug effects, cell penetration, tissue penetration, metabolism, bioavailability, excretion, absorption, drug-protein binding, drug-lipid interaction, drug-Deoxyribonucleic acid (DNA)/Ribonucleic acid (RNA) interaction, metabolite prediction, tissue distribution and/or any other suitable property, characteristic and/or trait in relation to a compound.

Preferably, the step of retraining the selection model further comprising retraining the selection model based on the property model score and the prediction result list. As an option, retraining the selection model based on the prediction result list further comprises retraining the selection model based on one or more discrepancies between validation results associated with the validation of the shortlist of compounds and the current or previous prediction result list(s) output from the current or previous property model(s). Preferably, wherein using the prediction result list to retrain the selection model comprises retraining the selection model based on the structures of compounds the property model is likely to incorrectly predict.

Preferably, the ML technique for generating and/or updating the property model is trained or updated based on a labelled training dataset comprising data representative of a subset or set of a plurality of compounds and their known association with the particular property. The ML technique for generating and/or updating the selection model is trained or updated based on a property model score and/or the prediction result list output from the property model based on a plurality of compounds. The property model score being a measure of the performance (e.g. predictive performance) of the property model when given a test set of a labelled training dataset after the property model has been trained.

Preferably, the method of generating the selection model may be repeated until it is determined the selection model has been validly trained. Additionally, the method may include further training the selection model by iterating over the steps including: receiving the prediction result list; retraining or updating the selection model; selecting a shortlist of compounds; sending the shortlist for validation in which the validation results are used to update the property model; an updated property model from a previous or current iteration is used when repeating these method steps for the next iteration. Iterating over these steps is performed until it is determined the selection model has been validly trained or when a stopping criterion has been reached or met. For example, the selection model may be determined to be validly trained by analysing the convergence or divergence of property model score(s) of the updated property model in each iteration. When the property model score does not substantially change to one or more previous and recent property model scores when computer analysis or laboratory experimentation is performed on the selected shortlist of compounds, then the selection model may be considered to be validly trained. In another example, a stopping criterion may include a maximum number of iterations having been achieved.

In a second aspect, the present disclosure provides an apparatus for generating a selection model based on a ML technique, the selection model for selecting a shortlist of compounds requiring validation with a particular property, the apparatus configured to: receive a prediction result list output from a property model for predicting whether a plurality of compounds are associated with a particular property and an property model score; retrain or update the selection model based on the property model score and/or the prediction result list; select a shortlist of compounds using the retrained/updated selection model from the plurality of compounds associated with the prediction result list; send the selected shortlist of compounds for validation with the particular property, wherein another ML technique is used to update the property model based on the validation; repeat at least the receiving and retraining of the selection model until determining the selection model has been validly trained.

In a second aspect, the present disclosure provides an apparatus comprising a processor, a memory unit and a communication interface, wherein the processor is connected to the memory unit and the communication interface, wherein the processor, communication interface and/or memory unit are configured to implement the computer-implemented method according to any of the first aspect, modification(s) thereof, and/or as described herein.

In a third aspect, the present disclosure provides a ML model comprising data representative of a ML selection model generated according to the computer-implemented method of any of the first aspect, modification(s) thereof, and/or as described herein.

In a fourth aspect, the present disclosure provides a ML selection model obtained or obtainable from a computer-implemented method according to any of the first aspect, modification(s) thereof, and/or as herein described.

In a fifth aspect, the present disclosure provides an apparatus comprising a processor, a memory unit and a communication interface, wherein the processor is connected to the memory unit and the communication interface, wherein the processor and memory are configured to implement a ML selection model according to any of the third or fourth aspects, modification(s) thereof, and/or as described herein.

In a sixth aspect, the present disclosure provides a computer-readable medium comprising data or instruction code representative of a ML selection model generated based on training a ML technique according to the computer-implemented method as described in any of the first aspect, modification(s) thereof, and/or as herein described, which when executed on a processor, causes the processor to implement the ML selection model.

In a seventh aspect, the present disclosure provides a computer readable medium comprising data or instruction code representative of a ML selection model according to any of the first, third or fourth aspects, modification(s) thereof, and/or as described herein, which when executed on a processor, causes the processor to implement the ML selection model.

In a eighth aspect, the present disclosure provides a ML validation model obtained or obtainable from the computer-implemented method of any of the first aspect, modification (s) thereof, and/or as herein described.

In an ninth aspect, the present disclosure provides a ML selection and validation model obtained or obtainable from the computer-implemented method of any of the first aspect, third, fourth or eighth aspects, modification(s) thereof, and/ or as herein described.

In an tenth aspect, the present disclosure provides a computer-implemented method for updating a property model, the property model for predicting whether a compound is associated with a particular property, the method comprising: generating a result list of compounds using the property model on a plurality of compounds; selecting a shortlist of compounds from the plurality of compounds using a selection model according to any of the first aspect, third, fourth, or eighth aspects, modifications thereof, and/or as herein described; receiving validation results for the shortlist of compounds; and updating the property model based on the validation results.

Preferably, the method further comprising repeating the steps of generating, selecting and receiving until the property model is determined to be validly trained.

Preferably, the method further comprising: validating the association each of the shortlist of compounds has with the particular property, wherein validating outputs validation results comprising data representative of further labelled training data corresponding to the validated property associations of each compound in the shortlist of compounds.

Preferably, wherein the property model is updated based on training a machine learning technique based on a labelled training dataset corresponding to multiple compounds and their association with a particular property.

In an eleventh aspect, the present disclosure provides an apparatus comprising a processor, a memory unit and a communication interface, wherein the processor is connected to the memory unit and the communication interface, wherein the processor, communication interface and/or memory unit are configured to implement the computer-implemented method according to any of the tenth aspect, modification(s) thereof, and/or as described herein.

In a twelfth aspect, the present disclosure provides a system for generating a selection model based on a ML technique, the selection model configured to select a shortlist of compounds for validation with a particular property, the system comprising: a selection module or apparatus according to any of the first to ninth aspects, modifications thereof, and/or as described herein for selecting a shortlist of compounds; and a ML/property updating module or apparatus according to any of the eleventh or twelfth aspects, modification(s) thereof, and/or as described herein, the property updating module or apparatus coupled to the selection module, wherein the property updating module or apparatus is configured to update the property model based on the selected shortlist of compounds.

In a thirteenth aspect, the present disclosure provides a system comprising: an property model generation module configured for generating a property model based on a labelled training dataset, the labelled training dataset comprising data representative of compounds associated with a particular property; an ML test module configured for generating a prediction result list output from the generated property model for predicting whether a plurality of compounds are associated with a particular property and a property model score associated with the predictions; and a selection module configured according to any one of the first to ninth aspects for selecting a shortlist of compounds from the prediction result list for validation, wherein validating the shortlist of compounds outputs validation results for updating the property model.

Preferably, the property model generation module is further configured to receive a further labelled training dataset based on the validation results of the shortlist of compounds, and update the property model by generating a property model based on the labelled training dataset and the further labelled training dataset.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously.

This application acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

The preferred features may be combined as appropriate, as would be apparent to a skilled person, and may be combined with any of the aspects of the invention.

BRIEF DESCRIPTION OF THE DRAWINGS

Embodiments of the invention will be described, by way of example, with reference to the following drawings, in which:

FIG. 2 is a table illustrating an example prediction result list output from a property model for a plurality of compounds for input to the training process(es) of FIGS. 1b and 1c according to the invention;

Figure 1A:
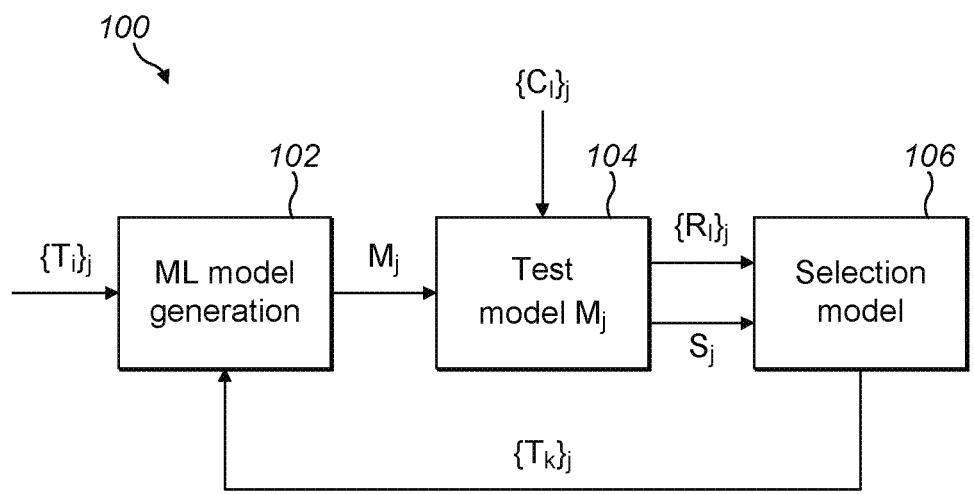
FIG. 1a is a schematic diagram illustrating an example training apparatus/system for training a selection model to predict a shortlist of compounds according to the invention.

Common reference numerals are used throughout the figures to indicate similar features.

DETAILED DESCRIPTION

Embodiments of the present invention are described below by way of example only. These examples represent the best mode of putting the invention into practice that are currently known to the Applicant although they are not the only ways in which this could be achieved. The description sets forth the functions of the example and the sequence of steps for constructing and operating the example. However, the same or equivalent functions and sequences may be accomplished by different examples.

The inventors have advantageously developed a selection method/mechanism that generates a selection model for predicting the best selection of a shortlist of compounds from a prediction result list of a machine learning (ML) model e.g. ML models such as, by way of example only but not limited to, property models for predicting whether a compound exhibits or has a particular property. The selection mechanism uses an iterative and semi-automated/automated approach to train a reinforcement learning (RL) technique to generate a selection model for predicting the best selection of a shortlist of compounds. The selection model assists in enhancing the training of ML techniques for generating accurate and reliable property models for predicting whether a compound exhibits or has a particular property. The generated selection model and selection method/mechanism may be particularly applicable when there is insufficient labelled training data for training the ML technique to generate a property model for predicting whether a compound has a particular property. The selection model can be used to enhance the labelled training dataset by selecting the best subset or shortlist of compounds for validation from a prediction result list of the property model that can further enhance the property model. For example, the validation results corresponding to the shortlist of compounds can be used to generate further labelled training data for use in updating the property model for maximising or at least improving its predictive performance. The selection mechanism may also learn to predict when to best validate the subset/shortlist against the particular property via computer analysis or via laboratory experimentation.

Although the following description of the invention refers to, by way of example only but is not limited to, property models and/or ML models for predicting whether one or more compound(s) is associated or has a particular property (e.g. whether one or more entities is associated with a relationship), it will be appreciated by the skilled person that the present invention may be applied to other ML models for predicting whether an entity or input data has a particular relationship with another entity, or for classifying one or more entities and/or input data according to a particular relationship etc. The entities may include one or more compound(s), molecule(s), drug(s), target(s), protein(s)/gene(s) or other biological entity and the like.

A predictive property model (or ML model for predicting whether a compound exhibits or has a particular property) can be configured to receive a compound as input and output data representative of a prediction for whether or not that compound has a particular property. For example, the property model may be configured to, by way of example only but is not limited to, predict whether a compound will bind to a particular protein; or whether the compound is soluble in water; or predict whether the compound is toxic to the human body or part of the human body; or predict any other property of interest in relation to compounds. However, the labelled training dataset may only contain data related to a few hundreds to a few thousand compounds in relation to the particular property. This is not enough data to properly train a ML technique to generate a property model that would predict whether a compound exhibits and/or has the particular property.

The quality of the property model may be improved by increasing the size of the labelled training dataset. For example, a plurality of compounds with an unknown association with the particular property may be tested in a laboratory via experimentation to measure whether or not they exhibit or are associated with the particular property. However, this is extremely costly for all but a few compounds. The inventors have developed a technique for limiting the number of compounds that are necessary to test in the laboratory whilst improving on the property model quality. This can be achieved by using a RL technique to iteratively learn to predict how to select a shortlist of compounds from a prediction result list of a plurality of compounds output from the property model that most effectively enhances the quality of the property model when retrained. The RL technique may also iteratively learn to predict what validation method should be used, for example, whether computer analysis or laboratory experimentation should be used to validate the shortlist of compounds in relation to the particular property.

Assuming the selection model has been trained to suitable select a shortlist of compounds and/or the validation method (e.g. computer analysis or laboratory experimentation), the selection model may be used to select a shortlist of compounds each time a property model is presented with a plurality of compounds most of which the property model might not have seen before (i.e. not part of the labelled training dataset used to initially train the property model). Typically, the selected shortlist may be greater than the number of compounds that are usually sent for testing in a laboratory. Computer analysis such as, by way of example only but not limited to, computer simulations based on atomistic and/or physical molecule interaction simulations (e.g. Molecular Dynamics®) may be used to validate the selected shortlist of compounds in relation to the particular property. This assumes the particular property may be simulated. The validation results of the shortlist are fed back into the property model (e.g. using them to enhance the labelled training dataset and for retraining or updating the property model accordingly), which may output another prediction result list based on the plurality of compounds or another plurality of compounds. The selection model further predicts another shortlist for validation by simulation and fed back into the property model. These steps may be repeated until the selection model predicts a shortlist suitable for laboratory testing for further enhancing the quality of the property model. After laboratory testing, the laboratory results of the validated shortlist of compounds may be fed back into the property model (e.g. the laboratory results are used to further enhance the labelled training dataset and retrain the property model accordingly). The steps may be repeated to select a shortlist of compounds for either computer analysis and/or laboratory experimentation until it is considered the property model has been suitably trained.

A compound (also referred to as one or more molecules) may comprise or represent a chemical or biological substance composed of one or more molecules (or molecular entities), which are composed of atoms from one or more chemical element(s) (or more than one chemical element) held together by chemical bonds. Example compounds as used herein may include, by way of example only but are not limited to, molecules held together by covalent bonds, ionic compounds held together by ionic bonds, intermetallic compounds held together by metallic bonds, certain complexes held together by coordinate covalent bonds, drug compounds, biological compounds, biomolecules, biochemistry compounds, one or more proteins or protein compounds, one or more amino acids, lipids or lipid compounds, carbohydrates or complex carbohydrates, nucleic acids, deoxyribonucleic acid (DNA), DNA molecules, ribonucleic acid (RNA), RNA molecules, and/or any other organisation or structure of molecules or molecular entities composed of atoms from one or more chemical element(s) and combinations thereof.

Each compound has or exhibits one or more property(ies), characteristic(s) or trait(s) or combinations there of that may determine the usefulness of the compound for a given application. The property of a compound or property of interest may comprise or represent data representative of or indicative of a particular behaviour of a compound when the compound undergoes a reaction. For example, a compound may be associated or exhibit one or more characteristics or properties, which may include by way of example only but is not limited to, one or more characteristics or properties from the group of: an indication of the compound docking with another compound to form a stable complex; an indication associated with a ligand docking with a target protein, wherein the compound is the ligand; an indication of the compound docking or binding with one or more target proteins; an indication of the compound having a particular solubility or range of solubilities; an indication of the compound having particular electrical characteristics; an indication of the compound having a toxicity or range of toxicities; any other indication of a property or characteristic associated with a compound that can be simulated using computer simulation(s) based on physical movements of atoms and molecules; any other indication of a property or characteristic associated with a compound that can be tested by experiment or measured. Further examples of one or more compound property(ies), characteristic(s), or trait(s), may include, by way of example only but are not limited to, one or more of: Log, Log D, solubility, toxicity, drug-target interaction, drug-drug interaction, off-target drug effects, cell penetration, tissue penetration, metabolism, bioavailability, excretion, absorption, drug-protein binding, drug-lipid interaction, drug-DNA/RNA interaction, metabolite prediction, tissue distribution and/or any other suitable property, characteristic and/or trait in relation to a compound.

Given a property of a compound may include data representative of or indicative of a particular behaviour/characteristic/trait of a compound when a compound undergoes a reaction, this data representative or indicative of the property of the compound may include, by way of example only but is not limited to, any continuous or discrete value/score and/or range of values/score(s), series of values/scores, strings or any other data representative of the property. For example, a property may be associated with, assigned, represented by, or is based on, by way of example only but not limited to, one or more continuous property value(s)/score(s) (e.g. non-binary values), one or more discrete property value(s)/score(s) (e.g. binary values), one or more range(s) of continuous property values/scores, one or more range(s) of discrete property value(s)/score(s), a series of property value(s)/score(s), one or more string(s) of property values, or any other suitable data representation of a property value/score representing a property and the like. The property value/score may be based on measurement data or simulation data associated with the reaction and/or the particular property.

A compound may be assigned a property value/score comprising data representative of whether or not they are associated with a particular property when the compound undergoes a reaction associated with the particular property. This property value/score may be determined or based on, by way of example only but is not limited to, laboratory measurement(s) and/or computer simulated value(s)/score (s). The property value/score assigned to the compound gives an indication of whether that compound is associated with or exhibits the particular property. For example, a compound may be assigned a property value/score depending on whether the compound exhibits a particular property when it undergoes a reaction associated with the particular property. The compound may be said to exhibit the particular property when the property value/score associated with the compound is, by way of example only but is not limited to, above or below a threshold property value/score representing the property, within a region or in the vicinity of a value representative of the property, and the like The property model generated for predicting whether a compound has one or more property(ies) according to the invention as described herein may be generated using one or more or a combination of ML techniques. A ML technique may comprise or represent one or more or a combination of computational methods that can be used to generate analytical models and algorithms that lend themselves to solving complex problems such as, by way of example only but is not limited to, prediction and analysis of complex processes and/or compounds. ML techniques can be used to generate property models for use in the drug discovery, identification, and/or optimization in the informatics, cheminformatics and/or bioinformatics fields.

For example, an ML technique may be trained using labelled training datasets to generate an ML model (e.g. a property model for predicting whether a compound has a particular property). A labelled training dataset that includes data representative of one or more compounds each of which may be labelled with data representative of a known property value/score or label associated with the compound and the particular property may be used by the ML technique to generate a property model. Thus, once the ML technique has trained an ML model based on such a labelled training dataset in relation to the particular property, the resulting trained ML model may be called a property model. The property model may thus predict or classify whether an input compound exhibits a particular property. The property model may output data representative of a property value/score representing the input compound's association with the particular property. The data representative of the property value/score output by the property model may be referred to herein as a property prediction value/score. The data representative of one or more compounds may be input to the property model, which may output property prediction values/scores comprising data representative of one or more corresponding property value(s)/score(s) indicative of whether the one or more input compounds are associated or exhibit the particular property modelled by the property model.

Examples of ML technique(s) that may be used to generate an ML model or a property model for predicting whether a compound has a particular property may include, by way of example only but is not limited to, a least one ML technique or combination of ML technique(s) from the group of: a recurrent neural network; convolutional neural network; reinforcement learning algorithm(s); and any other neural network structure configured for predicting whether a compound has a particular property.

Further examples of ML technique(s) that may be used as described herein according to the invention may include or be based on, by way of example only but is not limited to, any ML technique or algorithm/method that can be trained or adapted to generate one or more candidate compounds based on, by way of example only but is not limited to, an initial compound, a list of desired property(ies) of the candidate compounds, and/or a set of rules for modifying compounds, which may include one or more supervised ML techniques, semi-supervised ML techniques, unsupervised ML techniques, linear and/or non-linear ML techniques, ML techniques associated with classification, ML techniques associated with regression and the like and/or combinations thereof. Some examples of ML techniques may include or be based on, by way of example only but is not limited to, one or more of active learning, multitask learning, transfer learning, neural message parsing, one-shot learning, dimensionality reduction, decision tree learning, association rule learning, similarity learning, data mining algorithms/methods, artificial neural networks (NNs), deep NNs, deep learning, deep learning ANNs, inductive logic programming, support vector machines (SVMs), sparse dictionary learning, clustering, Bayesian networks, representation learning, similarity and metric learning, sparse dictionary learning, genetic algorithms, rule-based machine learning, learning classifier systems, and/or one or more combinations thereof and the like.

Some examples of supervised ML techniques may include or be based on, by way of example only but is not limited to, ANNs, DNNs, association rule learning algorithms, a priori algorithm, case-based reasoning, Gaussian process regression, group method of data handling (GMDH), inductive logic programming, instance-based learning, lazy learning, learning automata, learning vector quantization, logistic model tree, minimum message length (decision trees, decision graphs, etc.), XGBOOST, Gradient Boosted Machines, nearest neighbour algorithm, analogical modelling, probably approximately correct learning (PAC) learning, ripple down rules, a knowledge acquisition methodology, symbolic machine learning algorithms, support vector machines, random forests, ensembles of classifiers, bootstrap aggregating (BAGGING), boosting (meta-algorithm), ordinal classification, information fuzzy networks (IFN), conditional random field, anova, quadratic classifiers, k-nearest neighbour, boosting, sprint, Bayesian networks, Naïve Bayes, hidden Markov models (HMMs), hierarchical hidden Markov model (HHMM), and any other ML technique or ML task capable of inferring a function or generating a model from labelled and/or unlabelled training data and the like.

Some examples of unsupervised ML techniques may include or be based on, by way of example only but is not limited to, expectation-maximization (EM) algorithm, vector quantization, generative topographic map, information bottleneck (IB) method and any other ML technique or ML task capable of inferring a function to describe hidden structure and/or generate a model from unlabelled data and/or by ignoring labels in labelled training datasets and the like. Some examples of semi-supervised ML techniques may include or be based on, by way of example only but is not limited to, one or more of active learning, generative models, low-density separation, graph-based methods, co-training, transduction or any other a ML technique, task, or class of unsupervised ML technique capable of making use of unlabeled datasets and/or labelled datasets for training and the like.

Some examples of artificial NN (ANN) ML techniques may include or be based on, by way of example only but is not limited to, one or more of artificial NNs, feedforward NNs, recursive NNs (RNNs), Convolutional NNs (CNNs), autoencoder NNs, extreme learning machines, logic learning machines, self-organizing maps, and other ANN ML technique or connectionist system/computing systems inspired by the biological neural networks that constitute animal brains. Some examples of deep learning ML technique may include or be based on, by way of example only but is not limited to, one or more of deep belief networks, deep Boltzmann machines, DNNs, deep CNNs, deep RNNs, hierarchical temporal memory, deep Boltzmann machine (DBM), stacked Auto-Encoders, and/or any other ML technique.

Although a set of selection and/or validation rules may be derived for selecting a shortlist of compounds and/or selecting a validation method as described herein for validating the shortlist of compounds, a selection model may instead be generated based on training a reinforcement learning technique. The selection model is for predicting a shortlist of compounds suitable for validation in relation to the particular property. Thus, instead of using a set of selection rules to select an appropriate shortlist of compounds that the property model is uncertain about, an RL technique may be trained over time to make this selection. Once the RL technique has learnt to select a shortlist of compounds for enhancing the property model, the generated selection model may be used for training property models that are used to predict whether a compound exhibits or has a different property to the particular property. This is because the selection model does not depend on the type of property that each property model is modelling to predict.

An RL technique can be trained to learn what compounds from a result prediction list to select in order to maximise the quality of selection and generate a selection model. The quality of selection may be maximised when the selected shortlist of compounds are the best compounds to pick from that particular result prediction list, that when validated in relation to the particular property to maximise quality of the resulting updated property model. RL technique may be used to iteratively train a selection model that is robust enough to select the most appropriate or best shortlist of compounds from a result prediction list for validation in relation to the particular property.

The RL technique as described herein may be based on, by way of example only but is not limited to, at least one ML technique or combination of ML technique(s) from the group of: a recurrent neural network; convolutional neural network; reinforcement learning algorithm; any other neural network structure suitable for use in training an RL technique to generate a selection model as described herein; and/or any other ML or RL structure suitable for use in training an RL technique to generate a selection model as described herein.

FIG. 1a is a schematic diagram illustrating an example training apparatus 100 for generating a selection model based on a RL technique, the selection model for selecting, from a prediction result list, a shortlist of compounds requiring validation with a particular property. The prediction result list may be output from a property model for predicting whether a plurality of compounds are associated with a particular property. For example, the prediction result list may include a plurality of compounds, each of which are mapped to corresponding property prediction values/scores that are output/estimated by the property model. The training apparatus 100 implements an iterative feedback loop for training a selection model based on the RL technique during training or updating of a property model. The property model for predicting whether a compound is associated, exhibits or has a particular property. The training apparatus 100 includes a property model generation (MLG) device 102, Model evaluation (ME) device 104, selection mechanism (SM) 106, and feedback path 107. The MLG device 102 is configured for training an ML technique to generate or update the property model based on a first set of a labelled training dataset. The generated/updated or trained property model may be input to the ME device 104. The ME device 104 is configured for testing and evaluating the property model based on compounds from a second set of the labelled training dataset in which the first and second sets of the labelled training datasets are different. The SM 106 is configured for generating a selection model based on training an RL technique using an property model score. The SM 106 feeds back a further labelled training dataset via feed back path 107 based on the selected shortlist of compounds, which are validated against the second set of the labelled training dataset to form the further labelled training dataset. The property model is updated based on the an ML technique for updating the property model for a further iteration of the training.

In particular, initially in the first iteration, the MLG device 102 receives a labelled training dataset $\{T_i\}_j$ for $1<=i<=N$, where N is the number of training data elements (e.g. in the region of 1000s or more) in which the i-th training data element includes data representative of a compound $C_i$ and its known association with the particular property. The MLG device 102 may train an ML technique (this may be predetermined) using a first set of the labelled training dataset $\{T_i\}_j^1$ for $1<=i<=K$ to generate a property model $M_j$ for the j-th iteration. The property model $M_j$ predicts whether an input compound $C_l$ has a particular property. A second set of the labelled training dataset $\{T_i\}_j^2$ for $1<=i<=L$, where $N=L+K$, is set aside for training the RL technique to generate the selection model.

The ME device 104 receives the generated property model $M_j$, inputs a plurality of compounds $\{C_i\}_j$ to the property model $M_j$, where $1<=k=L$ and L is the number of the plurality of compounds. In this case, the plurality of compounds $\{C_i\}_j$ for $1<=l<=L$ are the compounds that are associated with the second set of the labelled training dataset $\{T_i\}_j^2$ for $1<=i<=L$. The property model M thus outputs a prediction result list $\{R_l\}_j$ for $1<=l<=L$, where the l-th prediction result $R_{l,j}$ for the j-th iteration may include, by way of example only but is not limited to, data representative of the compound $C_l$ and a prediction score $P_{l,j}$ for the j-th iteration. The prediction score $P_{l,j}$ being a value that represents the property model's $M_j$ prediction that compound $C_l$ is associated with the particular property. The prediction result list $\{R_l\}_j$ predicts whether each of the plurality of compounds $\{C_i\}_j$ has the particular property.

The ME device 104 also calculates a property model score $S_j$ that estimates the quality of the property model $M_j$ based on the prediction result list $\{R_l\}_j$ and/or the second set of labelled training dataset $\{T_i\}_j^2$. The property model score $S_j$ may be calculated based on model performance statistics that can be estimated from the labelled training dataset $\{T_i\}_j$, second labelled training dataset $\{T_i\}_j^2$ and/or received prediction result list $\{R_l\}_j$ 200. Model performance statistics may comprise or represent an indication of the performance of a property model based on labelled training dataset $\{T_i\}_j$, second labelled training dataset $\{T_i\}_j^2$ and/or received prediction result list(s) $\{R_l\}_j$ 200. The model performance statistics for a property model may be based on, by way of example, but is not limited to, one or more from the group of: positive predictive value or precision of the property model; sensitivity, true predictive rate, or recall of the property model; a receiver operating characteristic, ROC, graph associated with the property model; an area under a precision and/or recall ROC curve associated with the property model; any other function associated with precision and/or recall of the property model; and any other model performance statistic(s) for use in generating a property model score $S_j$ indicative of the performance of the property model.

The RL technique of the selection mechanism 106 can be taught which compounds of the prediction result list $\{R_l\}_j$ may be the best to select for validation and thus generates a selection model. Initially, the selection mechanism 106 may have only initialised the selection model, which is yet to be trained by the RL technique, so may initially select a "random" set of compounds from the result prediction list $\{R_l\}_j$ as a selected shortlist of compounds. The selected shortlist of compounds are validated against the second set of the labelled training dataset $\{T_i\}_j^2$ to form shortlist labelled training dataset $\{T_k\}_j$. This is achieved because the result prediction list $\{R_l\}_j$ is generated by the property model $M_j$ using compounds $\{C_l\}$ from the second set of the labelled training dataset $\{T_i\}_j^2$, the portion of the second set of labelled training dataset $\{T_i\}_j^2$ that corresponds to the selected shortlist of compounds may be fed back via feedback path 107 for input as shortlist labelled training dataset $\{T_k\}_j$ to the MLG 102 for retraining/updating the property model $M_j$ om the next iteration. The training apparatus 100 then proceeds to implement the next iteration (e.g. j=j+1).

In the second iteration (e.g. j=2), the MLG device 102 may retrain the ML technique (this may be predetermined) using the first set of the labelled training dataset $\{T_i\}_j^1$ for 1<=i<=K and also the shortlist labelled training dataset $\{T_k\}_j$ output from the selection mechanism 106 to generate a property model $M_j$ for the j-th iteration. The ME device 104 receives the generated property model $M_j$ from MLG device 102, and inputs the plurality of compounds $\{C_l\}_j$ associated with the second set of the labelled training dataset $\{T_i\}_j^2$ for 1<=i<=L. The property model $M_j$ thus outputs a prediction result list $\{R_l\}_j$ for 1<=l<=L, where the l-th prediction result $R_{l,j}$ for the j-th iteration may include, by way of example only but is not limited to, data representative of the compound $C_l$ and a prediction score $P_{l,j}$ for the j-th iteration.

The ME device 102 also calculates another property model score S for estimating the quality and/or performance of the property model $M_j$ based on the prediction result list $\{R_l\}_j$ and/or the second set of labelled training dataset $\{T_i\}_j^2$. The property model score $\{S_k\}$ 1<=k<j from a previous iteration (e.g. k=j−1) may be compared with the property model score S; of the current iteration. The property model score(s) $\{S_k\}$ 1<=k<=j and the prediction result list $\{R_l\}_j$ may be fed to the selection mechanism 106. If the selection mechanism 106 determines that there is an improvement in quality/accuracy in the performance of the property model $M_j$ based on the property model score(s) $\{S_k\}$, then this is fed back to the RL technique as a reward. The selection model associated with the RL technique may be updated/retrained based on the reward. The updated selection model may then be used by the selection mechanism 106 to select another set of compounds from the result prediction list $\{R_l\}_j$ as the shortlist of compounds for validation. The selected shortlist of compounds are validated against the second set of the labelled training dataset $\{T_i\}_j^2$ to form shortlist labelled training dataset $\{T_k\}_j$. This is achieved because the result prediction list $\{R_l\}_j$ is generated by the property model $M_j$ using compounds $\{C_l\}$ from the second set of the labelled training dataset $\{T_i\}_j^2$, the portion of the second set of labelled training dataset $\{T_i\}_j^2$ that corresponds to the selected shortlist of compounds may be fed back via feedback path 107 for input as shortlist labelled training dataset $\{T_k\}_j$ to the MLG 102 for retraining/updating the property model $M_j$ in the next iteration. The training apparatus 100 then proceeds to implement the next iteration (e.g. j=j+1).

However, if the selection mechanism 106 determines that the comparison of two or more property model score(s) $\{S_k\}$ 1<=k<=j results in there not being an improvement in quality/accuracy in the performance of the property model $M_j$ then this is fed back to the RL technique as a penalty. The selection model associated with the RL technique may be updated/retrained based on the penalty. Given that the property model $M_j$ has worsened in performance, it may be reverted back to a previous property model $M_{j-1}$ to before the property model had poor performance. The selection model may then be used to select another set of compounds from the result prediction list $\{R_l\}_j$ as the shortlist of compounds for validation. The selected shortlist of compounds are validated against the second set of the labelled training dataset $\{T_i\}_j^2$ to form shortlist labelled training dataset $\{T_k\}_j$. This is achieved because the result prediction list $\{R_l\}_j$ is generated by the property model $M_j$ using compounds $\{C_l\}$ from the second set of the labelled training dataset $\{T_i\}_j^2$, the portion of the second set of labelled training dataset $\{T_i\}_j^2$ that corresponds to the selected shortlist of compounds may be fed back via feedback path 107 for input as shortlist labelled training dataset $\{T_k\}_j$ to the MLG 102 for retraining/updating the property model $M_j$ in the next iteration. The training apparatus 100 then proceeds to implement the next iteration (e.g. j=j+1).

The above apparatus 100 repeats this iterative feedback process multiple times until, by way of example only but not limited to, there are no more compounds that need to be selected for the shortlist of compounds; and/or the property model scores $\{S_k\}$ 1<=k<=j indicate that the performance of the ML technique has plateaued; or some other condition or criteria indicating that the selection model has been validly trained and may be used to select further short lists of compounds.

Figure 1B:
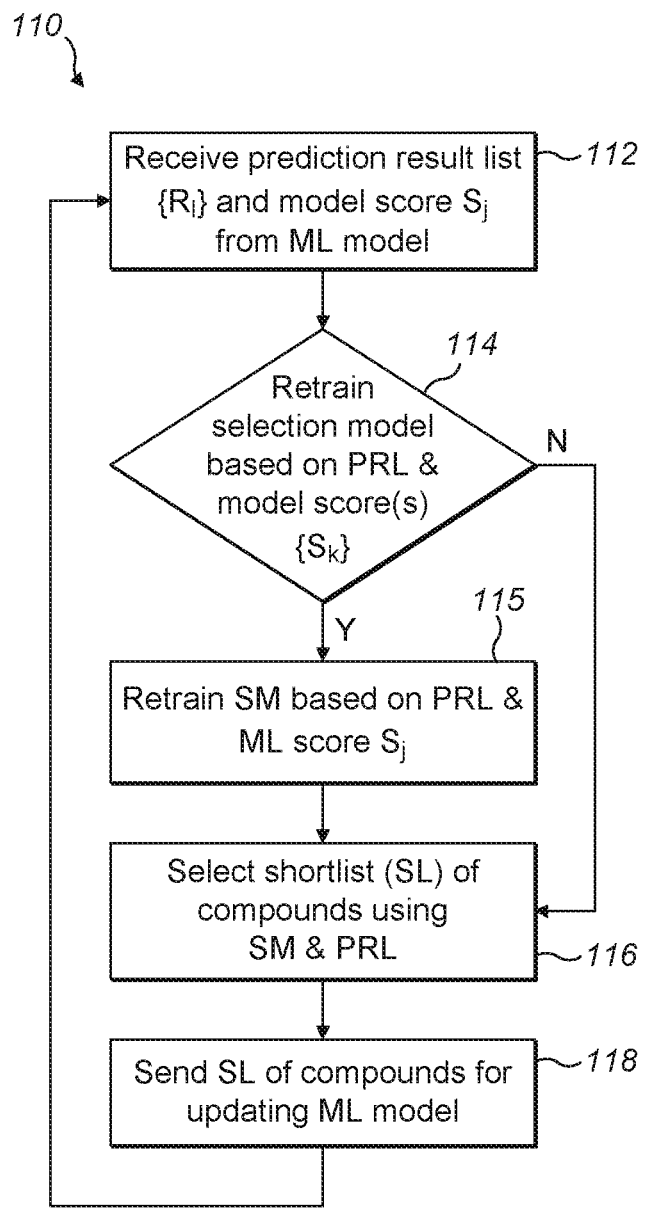
FIG. 1b is a flow diagram illustrating an example training process for use with the training apparatus of FIG. 1a according to the invention.

FIG. 1b is a flow diagram illustrating an example training process 110 for generating the selection model as described with reference to FIG. 1a. It is assumed an RL technique is trained to generate the selection model for predicting a shortlist of compounds that will enhance the further training of a property model. The property model for predicting whether a compound is associated with a particular property. The training process 110 may be implemented by selection mechanism 106 and/or training apparatus 100. The training process 110 may be as follows:

In step 112, a prediction result list is received from a property model for predicting whether a plurality of compounds are associated with a particular property and a property model score $S_j$. In step 114, it is determined whether to retrain the selection model based on the property model score, previous property model score(s) and/or the prediction result list. If it is determined to retrain the selection model (e.g. 'Y'), then the process proceeds to step 115. In step 115, the RL technique is retrained based on the property model score for the current iteration to generate an updated selection model. For example, if there is an improvement in property model score compared to the previous iteration, then the RL technique is rewarded during retraining, which positively affects the selection model. That is, the reward reinforces the RL technique to make selections of compounds that improve the performance of the property model. If there is not an improvement in property model score compared to the previous iteration, then the RL technique is penalised during retraining, which negatively impacts the selection model. That is the RL technique learns not to make the poorer selection. In step 116, the selection model, which may have been updated in step 115, is used to select a shortlist of compounds based on the prediction result list. In step 118, the selected shortlist of compounds are sent or fed back in the form of further labelled training dataset for use by an ML technique to update the property model. The steps of 112-118 may be repeated until it is determined that the selection model has been validly or sufficiently trained.

The training apparatus 100 and/or training process 110 may be used to initially bootstrap the generation of the selection model using only labelled training datasets. However, the labelled training datasets may be further enhanced using computer analysis/simulation and/or laboratory experiments to validate a selection of unknown compounds in relation to the particular property. This additional validation may also be used in the feedback path 107 for enhancing both the selection model and the property model $M_j$.

The property model $M_j$ may then be further trained, as described below, in which a plurality of compounds, most of which the property model has not seen before, may be input to the property model to generate a prediction result list $\{R_i\}_j$ in which the generated selection model may be used to select a shortlist of compounds for validation via computer analysis/simulation and/or laboratory experimentation in respect of the particular property. As described, the validation results may be used to generate further labelled training data that may be used to further update the property model and thus iteratively further improve the property model. In this process, the selection model may also be further trained by modifying the above training apparatus 100 to validate each selected shortlist of compounds in respect of the particular property using computer analysis/simulation, and/or on the rare occasion using laboratory experimentation. Property model scores may be calculated to allow the RL technique to reward or penalise the selection model during retraining.

Figure 1C:
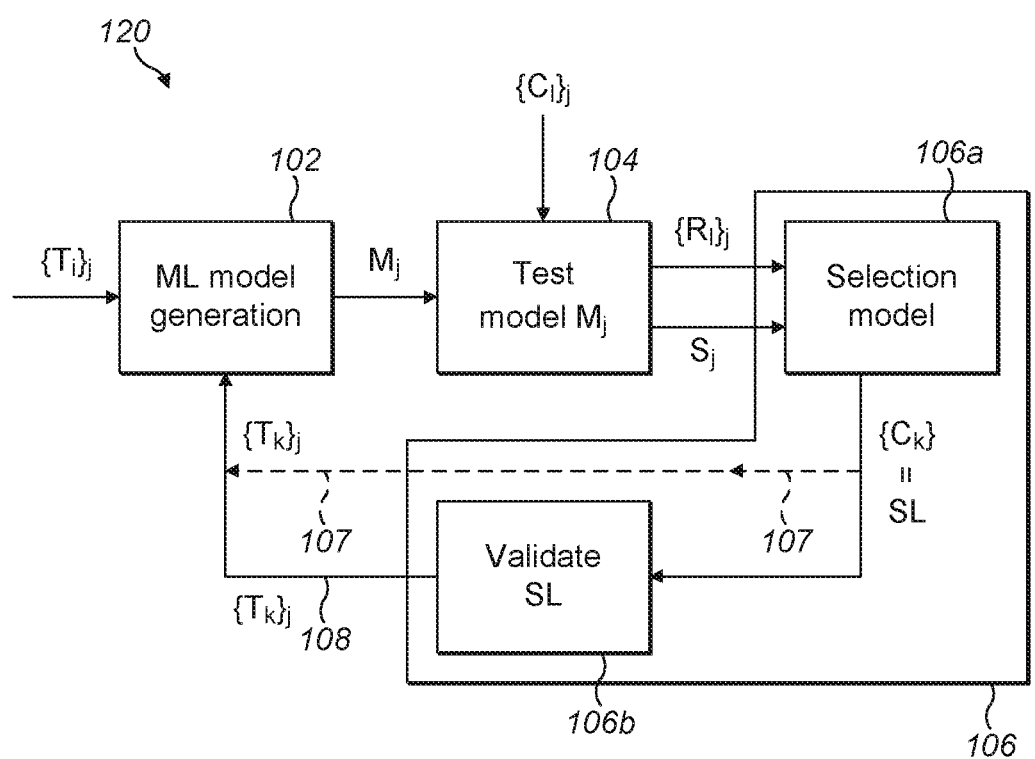
FIG. 1c is a schematic diagram illustrating another example training apparatus for training a selection model to predict a shortlist of compounds according to the invention for use in updating a property model to predict whether compounds have a particular property.

FIG. 1c is another schematic diagram based on FIG. 1a illustrating a further training apparatus 120 that is configured to selecting a shortlist of unknown compounds for validation in relation to the particular property for further enhancing the training of the RL technique for generating the selection model whilst also enhancing the training of the ML technique for generating the ML model $M_j$, which in this example is a property model for predicting whether a compound exhibits, is associated with, or has a particular property. The training apparatus 120 includes MLG device 102, ME device 104, SM 106 in which SM 106 includes selection model 106a and validation device 106b for validating the selected shortlist of compounds from the selection model in relation to the particular property. The validated selected shortlist of compounds are fed back in the form of a further labelled training dataset $\{T_k\}_j$. The property model is updated based on the further labelled training dataset $\{T_k\}_j$ for updating the property model for a further iteration of the training.

In particular, initially in the first iteration, the MLG device 102 receives a labelled training dataset $\{T_i\}_j$ for $1<=i<=N$, where N is the number of training data elements (e.g. in the region of 1000s or more) in which the i-th training data element includes data representative of a compound $C_i$ and its known association with the particular property. The MLG device 102 may train an ML technique (this may be predetermined) using this labelled training dataset $\{T_i\}_j$ to generate an property model $M_j$ for the j-th iteration. The property model $M_j$ is generated/updated to predict whether an input compound $C_l$ has a particular property.

Once the training of the ML technique has generated or updated the property model $M_j$ appropriately, the property model $M_j$ may be sent to the ME device 104. The ME device 104 receives the generated property model $M_j$ and inputs a plurality of compounds $\{C_l\}_j$ to the property model $M_j$, where $1<=l<=L$ and L is the number of the plurality of compounds. In this case, the plurality of compounds $\{C_l\}_j$ for $1<=l<=L$ may include a set or portion of compounds from the labelled training dataset $\{T_i\}_j$ but which also includes a set of compounds that have an unknown association or relationship with the particular property. The set of unknown compounds may be larger than the set of compounds from the labelled training dataset $\{T_i\}_j$. The property model $M_j$ thus outputs a prediction result list $\{R_l\}_j$ for $1<=l<=L$, where the l-th prediction result $R_{l,j}$ for the j-th iteration may include, by way of example only but is not limited to, data representative of the compound $C_l$ and a property prediction score $P_{l,j}$ for the j-th iteration. The property prediction score $P_{l,j}$ being a value that represents the property model's $M_j$ prediction of compound's $C_l$ association with the particular property. The prediction result list $\{R_l\}_j$ predicts whether each of the plurality of compounds $\{C_l\}_j$ has the particular property. For example, the prediction result list $\{R_l\}_j$ may include the plurality of compounds $\{C_l\}_j$ that were input to the property model $M_j$, in which each compound $C_l$ may be mapped or assigned a corresponding property prediction value/score, which may be output/estimated by the property model $M_j$ for each compound $C_l$ that is input.

The ME device 104 also calculates a property model score $S_j$ that estimates the quality of the property model $M_j$ based on the prediction result list $\{R_l\}_j$ and/or the labelled training dataset $\{T_i\}_j$. The property model score $S_j$ may be calculated based on model performance statistics that can be estimated from the labelled training dataset $\{T_i\}_j$ and/or received prediction result list $\{R_l\}_j$ 200. Model performance statistics may comprise or represent an indication of the performance of a property model based on labelled training dataset $\{T_i\}_j$ and/or received prediction result list(s) $\{R_l\}_j$ 200. The model performance statistics for a property model may be based on, by way of example, but is not limited to, one or more from the group of: positive predictive value or precision of the property model; sensitivity, true predictive rate, or recall of the property model; a receiver operating characteristic, ROC, graph associated with the property model; an area under a precision and/or recall ROC curve associated with the property model; any other function associated with precision and/or recall of the property model; and any other model performance statistic(s) for use in generating a property model score S; indicative of the performance of the property model.

The RL technique of the SM 106 can be taught which compounds of the prediction result list $\{R_l\}_j$ may be the best to select for validation and thus generates a selection model. Initially, the SM 106 may have only initialised the selection model 106a, which is yet to be trained by the RL technique, so may initially select a "random" set of compounds from the result prediction list $\{R_l\}_j$ as a selected shortlist of compounds. Alternatively the SM 106 may have bootstrapped the selection model 106a based on the training apparatus 100 and process 110 as described in FIGS. 1a and 1b using feedback path 107 and first and second sets of the labelled training dataset. In any event, the selection model 106a selects a shortlist of compounds for validation. Given that one or more of the selected shortlist of compounds may have an unknown association or relationship with the particular property, the selected shortlist of compounds are validated in relation to the particular property in validation device 106b.

Validation device 106b may validate one or more of the selected shortlist of compounds in relation to the particular property using either the labelled training dataset, computer analysis/simulation, and/or laboratory experimentation (or experiments) to establish the association each compound may have in relation to the particular property. The validation device 106b outputs shortlist labelled training dataset $\{T_k\}_j$ that provides an indication of the association of each of the shortlist of compounds with the particular property.

Given that the prediction result list $\{R_l\}_j$ is generated by the property model $M_j$ using compounds $\{C_l\}$, which may include multiple compounds from the labelled training dataset $\{T_i\}_j$ with a known association with the particular property, and also multiple compounds with an unknown association with the particular property, the selected shortlist of compounds may include one or more of the multiple compounds from the labelled training dataset $\{T_i\}_j$ and/or one or more of the multiple compounds with an unknown association with the particular property.

The validation device 106b may detect whether one or more of the selected shortlist of compounds includes one or more of the multiple compounds from the labelled training dataset $\{T_i\}_j$. If one or more of the multiple compounds from the labelled training dataset $\{T_i\}_j$ are detected in the shortlist, then these compounds may not need to be validated using computer analysis/simulation. The corresponding portion(s) of labelled training dataset $\{T_i\}_j$ may simply be added to the shortlist labelled training dataset $\{T_k\}_j$. If one or more of the multiple compounds in the shortlist have an unknown association with the particular property, i.e. they do not appear in the labelled training dataset used to train the property model $M_j$, then these compounds may be validated in relation to the particular property using computer analysis/simulation and/or, on occasion or when necessary, laboratory experimentation.

The validation results for these compounds may be used to generate further portion(s) of labelled training data elements for inclusion into the shortlist labelled training dataset $\{T_k\}_j$. The validation device 106b then forwards the shortlist labelled training dataset $\{T_k\}_j$ based on the selected shortlist of compounds via feedback path 108 for input as shortlist labelled training dataset $\{T_k\}_j$ to the MLG 102 for retraining/updating the property model $M_j$ in the next iteration. This shortlist of labelled training dataset $\{T_k\}_j$ may be incorporated into the original labelled training dataset $\{T_i\}_j$, which may be used to retrain the property model $M_j$. The training apparatus 100 then proceeds to implement the next iteration (e.g. j=j+1).

In the second iteration (e.g. j=2), the MLG device 102 may retrain or update the ML technique (this may be predetermined) using the enhanced labelled training dataset $\{T_i\}_j$, which is based on the previous labelled training dataset $\{T_i\}_j$ and the previous shortlist labelled training dataset $\{T_k\}_j$, to generate an updated property model $M_j$ for the j-th iteration. The ME device 104 receives the generated/updated property model $M_j$ from MLG device 102, and inputs the plurality of compounds $\{C_l\}_j$ for $1<=i<=L$. The plurality of compounds $\{C_l\}_j$ may be different from the previous iteration, or they may be the same. The property model $M_j$ thus outputs a prediction result list $\{R_l\}_j$ for $1<=l<=L$, where the l-th prediction result $R_{l,j}$ for the j-th iteration may include, by way of example only but is not limited to, data representative of the compound $C_l$ and a prediction score $P_{l,j}$ for the j-th iteration.

The ME device 102 also calculates another property model score S for estimating the quality and/or performance of the property model $M_j$ based on the prediction result list $\{R_l\}_j$ and/or the enhanced labelled training dataset $\{T_i\}_j$. The property model score $\{S_k\}$ $1<=k<j$ from a previous iteration (e.g. k=j−1) may be compared with the property model score $S_j$ of the current iteration. The property model score(s) $\{S_k\}$ $1<=k<=j$ and the prediction result list $\{R_l\}_j$ may be fed to the SM 106. If the SM 106 determines that there is an improvement in quality/accuracy in the performance of the property model $M_j$ based on the property model score(s) $\{S_k\}$, then this is fed back to the RL technique as a reward. The selection model 106a associated with the RL technique may be updated/retrained based on the reward. The updated selection model 106a may then be used by the selection mechanism 106 to select another set of compounds from the result prediction list $\{R_l\}_j$ as the shortlist of compounds for validation by validation device 106b. The selected shortlist of compounds are validated using validation device 106b to form shortlist labelled training dataset $\{T_k\}_j$ in a similar manner as described in the previous iteration. The shortlist labelled training dataset $\{T_k\}_j$ may be fed back via feedback path 108 for input as shortlist labelled training dataset $\{T_k\}_j$ to the MLG 102 for retraining/updating the property model $M_j$ in the next iteration. The training apparatus 100 then proceeds to implement the next iteration (e.g. j=j+1).

However, if the selection mechanism 106 determines that the comparison of two or more property model score(s) $\{S_k\}$ $1<=k<=j$ results in there not being an improvement in quality/accuracy in the performance of the property model $M_j$ then this is fed back to the RL technique as a penalty. The selection model 106a associated with the RL technique may be updated/retrained based on the penalty. Given that the property model $M_j$ has worsened in performance, it may be reverted back to a previous property model $M_{j-1}$ to before the property model had poor performance. The selection model 106a may then be used to select another set of compounds from the result prediction list $\{R_l\}_j$ as the shortlist of compounds for validation by validation device 106b. The selected shortlist of compounds are validated using validation device 106b to form shortlist labelled training dataset $\{T_k\}_j$ in a similar manner as described in the previous iteration. The shortlist labelled training dataset $\{T_k\}_j$ may be fed back via feedback path 108 for input as shortlist labelled training dataset $\{T_k\}_j$ to the MLG 102 for retraining/updating the property model $M_j$ in the next iteration. The training apparatus 100 then proceeds to implement the next iteration (e.g. j=j+1).

The above apparatus 120 repeats this iterative feedback process multiple times until, by way of example only but not limited to, there are no more compounds that need to be selected for the shortlist of compounds; the are no more compounds with unknown relationships with the particular property; and/or the property model scores $\{S_k\}$ $1<=k<=j$ indicate that the performance of the ML technique has plateaued; or some other condition or criteria indicating that the selection model 106a has been validly trained and may be used to select further short lists of compounds.

Figure 1D:
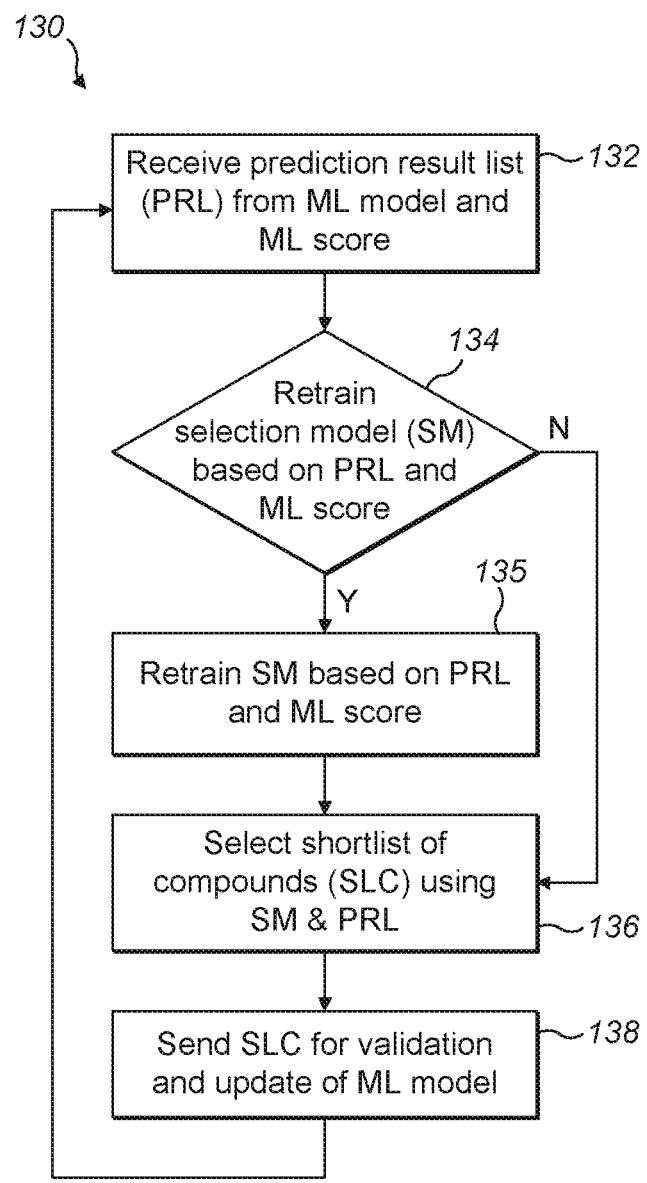
FIG. 1d is a flow diagram illustrating another example training process according to the invention for use with the training apparatus of FIG. 1c.

FIG. 1d is another flow diagram illustrating another example training process 130 for training a selection model to select a shortlist of compounds according to the invention and as described with reference to FIG. 1c. The selection model is generated by training an RL technique for predicting a shortlist of compounds that will enhance the further training of a property model. The training process 130 may be implemented by selection mechanism 106 and/or training apparatus 120. The selection model may initially be bootstrapped by using the training apparatus 100 and/or training process 110 as described previously in FIGS. 1a-1b. In such a case, the training process 130 may be used to further enhance the selection model and/or whilst property model is being further enhanced. It is also noted, that example training process 130 may also be used to train an RL technique from scratch to generate a selection model for selecting a shortlist of compounds for validation and further enhancing the training of the ML technique for generating the property model. The process 130 for training or retraining an RL technique to generate a selection model that may better predict a shortlist of compounds based on a result prediction list output from a property model Mj and/or a property model score Sj may include the following steps of:

In step 132, a prediction result list $\{R_i\}_j$ and the property model score $S_j$ for the current iteration j is received by the RL technique/selection model. In step 134, it is determined whether to retrain the selection model to select a set of compounds for the shortlist of compounds based on the property model score $S_j$ and/or previous property model score(s) $\{S_k\}$ for $1<=k<j$. For example, the property model score $\{S_k\}$ $1<=k<j$ from a previous iteration (e.g. k=j-1) may be compared with the property model score S; of the current iteration. If there is an improvement in quality/accuracy in the performance of the property model then this is fed back to the RL technique as a reward and the selection model may be retrained (e.g. 'Y') and the process proceeds to step 135. The property model may then be retained/kept for another iteration of training the selection model. If, in step 134, the comparison between property model scores $S_j$ and previous property model score(s) $\{S_k\}$ for $1<=k<j$ results in there not being an improvement in quality/accuracy in the performance of the property model in the current iteration, then this is fed back to the RL technique as a penalty and the selection model may be retrained (e.g. 'Y') then the process proceeds to step 135. If it is determined based on the prediction result list $\{R_i\}_j$, property model score $S_j$ and/or previous property model score(s) $\{S_k\}$ that retraining is unnecessary, then the process 130 proceeds to step 136.

In step 135, depending on the type of retraining the selection model associated with the RL technique may be updated/retrained based on the reward or the penalty. If the selection model associated with the RL technique is to be updated/retrained based on the penalty, then given that the property model has worsened in performance, the selection model may indicate to the ML technique that it should revert back to a previously retained/kept property model prior to when the property model had poor performance. Once the selection model has been retrained, the process 130 may proceed to step 136.

In step 136, the selection model may be used to select a set of compounds for the shortlist of compounds from a prediction result list output from the property model $M_j$ for validation of the shortlist of compounds. In step 138, the selection model sends the selected shortlist of compounds for validation and/or update of the property model. Validating the selected shortlist of compounds may include validating the association that each compound from the shortlist of compounds has with the particular property based on either labelled training datasets, laboratory experimentation and/or computer analysis. For example, laboratory experimentation may be performed on the shortlist of compounds to determine whether these exhibit or are associated with a particular property. The laboratory experimentation may output a set of laboratory experimental validation results in relation to the selected shortlist of compounds and the property. The property model may be updated based on the laboratory experimentation validation results and the ML technique for generating/updating the property model. Additionally or alternatively, computer analysis (e.g. simulations) may be performed on the shortlist of compounds to determine whether these exhibit or are associated with a particular property. The computer analysis (e.g. simulations) may output a set of computer analysis validation results in relation to the selected shortlist of compounds and the particular property. The property model may be updated based on the computer analysis validation results and the ML technique for generating/updating the property model.

The selected shortlist of compounds may be validated in relation to the particular property using computer analysis/simulation and/or laboratory experiments. Computer analysis/simulation may be used to validate whether each of the selected shortlist of compounds has the particular property. The computer analysis (e.g. simulations) may output a set of computer analysis validation results in relation to the selected shortlist of compounds and the particular property. On occasion, it may be determined, as described herein, to validate some or all of the selected shortlist of compounds via laboratory experimentation. The laboratory experimentation may output a set of laboratory experimental validation results in relation to the selected shortlist of compounds and the property. The property model may be updated based on the ML technique, the labelled training dataset and also the computer analysis validation results or the laboratory experimental validation results that validates the shortlist of compounds. That is, the validation results for the validated shortlist of compounds may be represented as further labelled training dataset associated with the shortlist of compounds, which may be used to further train the ML technique to generate/update the property model. A plurality of compounds $\{Cl\}$ $1<=l<=L$ may be input to the updated property model and a prediction result list $\{R_i\}_j$ and an property model score Sj may be output or generated. That is, an property model score S and further prediction result list $\{R_i\}_j$ may be generated based on the plurality of compounds $\{C_l\}$ $1<=l<=L$ input to the updated property model.

The selection model training process 130 may proceed to the next iteration (e.g. j=j+1) and step 132 in which the selection model receives another result prediction list and/or property model score $S_j$ from the updated property model.

In step 134, it may be determined that the selection model is fully trained and that further training does not necessarily improve the selection of the shortlist of compounds. For example, if no improvement can be seen in the predictive property model then the selection model may be considered to be trained and further training may be unnecessary. For example, one method of determining that the selection model is fully trained may include checking whether the selected shortlist of compounds sent for testing in the laboratory and/or by computer simulation do not make any subsequent predictive property model, generated by retraining the ML technique based on the laboratory or computer simulation results, worse and/or the same. Comparing previous property model scores with the current re-trained property model score may be useful in determining whether the selection model can be considered to be fully trained. For example, the selection model may be considered to be trained when comparing the retrained property model score with a previous retrained property model score(s) indicates a plateau of property model scores. The selection model may then be considered to be trained when comparing the current updated/retained property model score with previous retained/kept property model score(s) indicates a plateau of property model scores. In such a case, training process 130 may terminate and output the selection model for use in selecting shortlists of compounds for enhancing the training of other property models that are configured to predict whether a compound is associated with the particular property.

As described above, the validated shortlist of compounds may subsequently be used to enhance the training of a ML technique for generating a property model that predicts whether a compound exhibits or has the particular property.

The particular property may be based on one of a plurality of properties associated with compounds. The selection process 100 is based on reinforcement learning techniques that iteratively trains the selection model to predict the best or most suitable shortlist of compounds for validation by either computer analysis and/or laboratory experimentation/testing. The validation results can be used to further enhance a labelled training dataset used by an ML technique for generating and/or updating the property model so it can be used for a broad range of compounds. Once trained, the selection model may be stored and used for predicting shortlists of compounds requiring validation with any particular property of a plurality of properties.

Other modifications to the process 130 may include in response to determining to retrain the selection model in step 134, an indication may be sent to the ML technique for generating the updated property model to revert the property model to a previous property model when the property model score does not reach a property model performance threshold compared with the corresponding previous property model score. Alternatively or additionally, in step 134, an indication may be sent to the ML technique for generating the updated property model to retrain the property model $M_j$ rather than replace it with a previously trained property model when the property model score is indicative of meeting or exceeding the property model performance threshold compared with the corresponding previous property model score.

Further modifications may be made that allows the selection model to be trained by the RL technique to not only select a shortlist of compounds but to also select the validation method of using either computer analysis/simulation and/or laboratory experimentation. Given the cost of performing laboratory experimentation, it may be preferable to include a rule that penalises the RL technique when the selection model selects the validation method to be laboratory experimentation too early in the training process 130 or when there are still improvements to be made using computer analysis/simulation.

Additional modifications to the process 130 may be made such as, byway of example only but not limited to, in steps 134-135, when retraining of the selection model is to be performed, then using the prediction result list to retrain the selection model by showing the selection model or the RL technique for generating the selection model the discrepancy between the laboratory and/or computer analysis/simulation validation results and the original property model prediction results. This may essentially allow the selection model or the RL technique to learn which structures of compounds, molecules, or chemicals the property model is most likely to make an incorrect prediction on.

For example, in steps 134-135, when retraining of the selection model is determined, the retraining may further include retraining the selection model based on the property model score and the prediction result list. This may include using the prediction result list to identify one or more discrepancies between validation results associated with the validation of the shortlist of compounds and the current or previous prediction result list(s) output from the current or previous property model(s). Alternatively or additionally, using the prediction result list to retrain the selection model may further include retraining the selection model based on the structures of compounds the property model is likely to incorrectly predict.

In other modifications, the process 130 for generating the selection model may be repeated until it is determined the selection model has been validly trained. For example, the process 130 may include further training or updating the selection model by iterating over the steps 132-138, which includes: step 132 for receiving the prediction result list; step 134-135 for retraining or updating the selection model; step 136 for selecting a shortlist of compounds; and step 138 for sending the shortlist for validation in which the validation results are used to update the property model. In each iterations of these steps, an updated property model from a previous or current iteration may be used when repeating the process 130 for the next iteration. Iterating over these steps 132-138 may be performed until it is determined the selection model has been validly trained or when a stopping criterion has been reached or met. For example, the selection model may be determined to be validly trained by analysing the convergence or divergence of property model score(s) of the updated property model in each iteration. When the property model score does not substantially change to one or more previous and recent property model scores when computer analysis and/or laboratory experimentation is performed on the selected shortlist of compounds, then the selection model may be considered to be validly trained. In another example, a stopping criterion may include a maximum number of iterations having been achieved. It is to be appreciated by the skilled person that any other determination/consideration/criterion/criteria may be used for determining when the selection model is validly trained and/or for meeting a stopping criterion as the application demands.

FIG. 2 is a table illustrating an example prediction result list $\{R_l\}_j$ 200 for $1<=l<=L$ output from a property model for predicting whether a plurality of compounds $\{C_l\}$ for $1<=l<=L$ are associated with a particular property, which may be used as input to the selection model according to the invention. The property prediction value/score indicating a compound's association with a particular property $C_l$ may include data representative of a prediction score $P_l$. The prediction result list $\{R_l\}_j$ 200 includes data representative of the plurality of compounds $\{C_l\}$ 202 and their corresponding a prediction scores $\{P_l\}$ 204 (e.g. property prediction values/scores) for $1<=l<=L$. The plurality of compounds $\{C_l\}$ includes compounds $C_1, C_2, \ldots, C_l, \ldots, C_{L-1}, C_L$. The corresponding plurality of prediction scores $\{P_l\}$ 204 includes prediction scores $P_1, P_2, \ldots, P_l, \ldots, P_{L-1}, P_L$. Each prediction score $P_l$ indicates whether said each compound $C_l$ has or is associated with the particular property. The validation step 106 may select a shortlist of compounds from the prediction result list $\{R_l\}_j$ 200 based, at least in part, on the prediction scores.

As described previously, the prediction score comprises or represents data representative of a value representative or indicative of the ML Model predicting whether a compound has or has not a particular property. The prediction score may be a value, by way of example only but not limited to, a probability value, a certainty value or score, a percentage score or any other value that is indicative of representing the prediction of whether a compound has or has not the particular property, or a prediction of whether the compound exhibits or does not exhibit the particular property, and/or a prediction of how associated the compound is with the particular property; and/or any other value, score or statistic that is useful for assessing or classifying whether a compound is associated with a particular property and the like.

For example, the prediction score $P_l$ for whether compound $C_l$ is associated with a particular property may be represented as a certainty score value. Compounds that are known to have the particular property are given a value representing "positive" certainty score (e.g. $P_{CP}$). Compounds that are known not to have the particular property are given a value representing a "negative" certainty score (e.g. $P_{CN}$). Other compounds are given a value representing an "uncertainty" score ($P_I=X_I$, where $P_{CN}<X_I<P_{CP}$). The "uncertainty" score may be a continuous real value that represents the level of uncertainty the ML Model has in relation to whether that compound is associated with the particular property. The "uncertainty" score may have a continuous value that is between the value representing the positive certainty score and the value representing the negative certainty score (e.g. $P_{CN}<P_I<P_{CP}$). In the present example, the certainty score is represented as a percentage certainty score, where the positive certainty score is 100%, the negative certainty score is 0%, and the uncertainty score is between the positive and negative certainty scores i.e. between 0% and 100%.

In FIG. 2, the prediction result list $\{R_l\}_j$ 200 ranks the plurality of compounds $\{C_l\}$ 202 based on their prediction scores $\{P_l\}$ 204. For example, if a compound has or exhibits a particular property then the prediction score may have a positive level of certainty represented as a probability in the region of 1 or percentage score in the region of 100% (e.g. in the range of 0.85-1 or in the range of 85-100%). In FIG. 2, $C_1$ and $C_2$ have positive certainty scores represented as a percentage score of $P_{CP}$=100%, which means that the ML Model is 100% confident that these compounds $C_1$ and $C_2$ have the particular property. As well, $C_{L-1}$ and $C_L$ have negative certainty scores represented as a percentage score of $P_{CN}$=0%, which means that the ML Model is 100% confident that these compounds $C_{L-1}$ and $C_L$ do not have the particular property. There may be one or more or a plurality of compounds $\{C_l\}$ in which the prediction score has a value $P_I=X_I$ that is between $P_{CN}<P_I<P_{CP}$, where the ML Model has a continuum of confidence as to whether these compounds are associated with particular property. Of interest are those compounds located in a region midway between $P_{CN}$ and $P_{CP}$(e.g. 45%<$P_I$<55%), which include compounds that the property model predicts as being most uncertain as to whether these compounds are or are not associated with the particular property. It is these compounds that may be of interest for selecting in a shortlist of compounds that may be validated in relation to the particular property.

As an example, if the compound is reasonably known to have or does exhibit the particular property, then the prediction score $P_I$ for that compound may have a positive level of certainty represented as a probability in the region of 1 or a percentage score in the region of 100% (e.g. a probability in the range of 0.85-1 or a percentage score in the range of 85-100%). If the compound is reasonably known not to have or does not exhibit the particular property, then the prediction score $P_I$ for that compound may have a negative level of certainty represented as a probability in the region of 0 or percentage score in the region of 0% (e.g. a probability in the range of 0-0.15 or a percentage score in the range of 0-15%). Compounds with prediction scores in between the positive level of certainty and negative level of certainty may be considered to have a prediction score that is uncertain or be borderline. For example, those compounds with prediction scores with probability in the region of 0.5 or having a percentage score in the region of 50% (e.g. between 0.45 and 0.55 or between 45-55%) may be considered to be the most uncertain or the most borderline. That is, the property model cannot determine one way or the other whether these compounds have or have not (exhibit or do not exhibit) the particular property. It is these compounds that will be of interest to validate in relation to the particular property and so generate further labelled training datasets for updating the property model as described herein.

A rule set may be defined that selects what may be thought of as the best compounds from the prediction result list such as, by way of example only but not limited to, the topmost uncertain compounds from the prediction result list; the most structurally dissimilar compounds compared with the compounds associated with the labelled training dataset used to train the property model, along with many other combinations or rules. However, a rule set for selecting the shortlist of compounds may not yield the best selection of compounds that maximises the quality of any updated property models. Instead of defining a rule set for selecting a shortlist of compounds, training apparatus and process(as) 100, 110, 120 and 130 define the generation of a selection model by training an RL technique to select a shortlist of compounds that maximises or enhances the quality and/or accuracy of the property model. Using an RL technique allows the selection model to define a "rule set" that learns all the necessary nuances required for selecting the best shortlist of compounds at any given iteration of the training process that should or will enhance the training of the property model.

Figure 3:
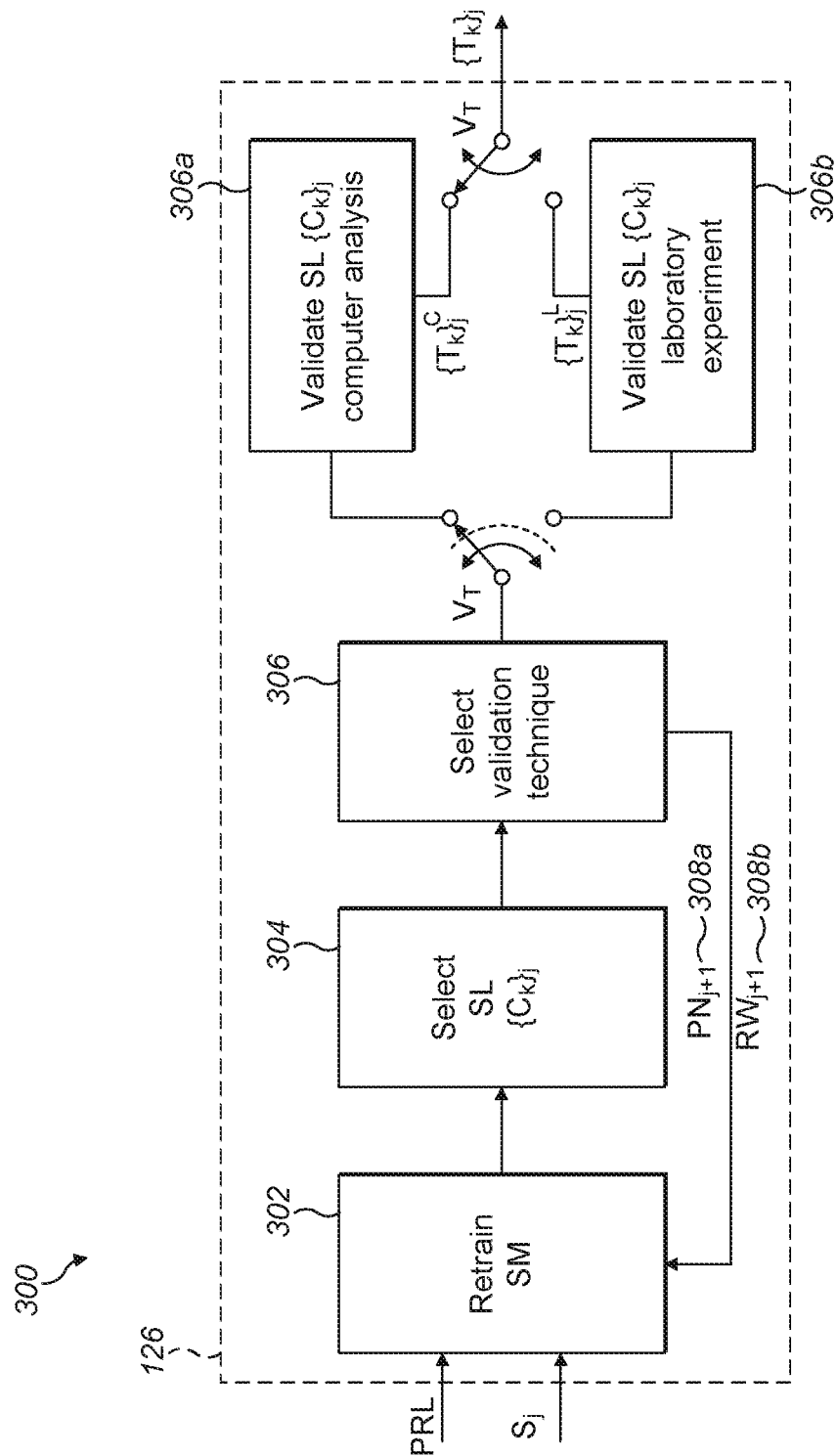
FIG. 3 is a schematic diagram illustrating another example selection apparatus for selecting and validating a shortlist of compounds according to the invention.

FIG. 3 is a schematic diagram illustrating an example selection mechanism 300 for selecting a shortlist of compounds and validation method according to the invention. The selection mechanism 300 may be used to further modify or replace selection mechanism 106, for selecting and validating a shortlist of compounds for use in training a ML technique to generate or update the property model. The selection mechanism 300 includes a retraining mechanism 302, a selection model 304, a validation selector 306, computer analysis validator 306a and laboratory validator 306b. Selection mechanism 300 receives at least a prediction result list $\{R_l\}_j$ 200, property model score $S_j$, and/or property model score(s) $\{S_k\}$ for 1<=k<j. The retraining mechanism 302 decides whether to retrain the selection model and validation model based, at least in part, on the prediction result list $\{R_l\}_j$ 200, property model score $S_j$, and/or property model score(s) $\{S_k\}$. The selection model 304 and validation selector 306 may predict, from the prediction result list prediction result list $\{R_l\}_j$ 200, a shortlist of compounds $\{C_k\}_j$ and validation method, which, when the shortlist is validated by either computer analysis validator 306a or laboratory validator 306b in relation to the particular property, should enhance the update of the property model $M_j$ on the next iteration of the training process 110 or 130.

The validation selector 306 may be configured to indicate, via a selector $V_T$ or some other technique/method, that computer analysis/simulation be selected such that the shortlist of compounds $\{C_k\}_j$ is directed/requested to be processed by the computer analysis validator 306a, which is used to validate the shortlist of compounds. The computer analysis validator 306a may be connected to one or more computer analysis/simulation systems (e.g. Molecular Dynamics (MD)®molecular simulator) that can atomistically simulate whether a compound has or exhibits a particular property. For example, MD simulator simulates the properties of compounds/molecules using atomistic and/or physical simulation of the molecules. The types of properties of compounds that may be simulated by MD includes, by way of example only but is not limited to, docking simulations including protein docking with the compound, and/or any other property or compound that can be simulated to determine whether the compound has the particular property.

The computer analysis/simulator validator 306a validates the shortlist by sending the shortlist to a computer analysis/simulation system that performs a computer analysis/simulation analysis based on the particular property and the shortlist of compounds $\{C_k\}_j$. The computer analysis/simulator validator 306a may receive the computer analysis/simulation results from the computer analysis/simulation system. The computer analysis/simulation results may be used to estimate the association each compound on the shortlist of compounds has with the particular property. The computer analysis/simulation results associated with the short list of compounds $\{C_k\}_j$ may be output in the form of a labelled training dataset $\{T_k\}_j^C$, which may be used to generate a further training dataset $\{T_k\}_j$ for use, as described herein, by ML technique in generating/updating the property model $M_j$. The selector $V_T$ may be used to select the labelled training dataset $\{T_k\}_j^C$ as the further training dataset $\{T_k\}_j$ for training the ML technique to generating/updating the property model $M_j$.

The validation selector 306 may be configured to indicate, via a selector $V_T$ or some other technique/method, that laboratory experimentation be selected such that the shortlist of compounds $\{C_k\}_j$ is directed/requested to be processed by the laboratory validator 306b for validating the shortlist of compounds. The laboratory validator 306b may be connected to one or more computer systems associated with one or more laboratory(ies) that can receive the shortlist of compounds and perform laboratory experiments in relation to whether each compound in the shortlist has or exhibits the particular property. The experimental results associated with the short list of compounds $\{C_k\}_j$ may be output in the form of a labelled training dataset $\{T_k\}_j^L$ Alternatively, the laboratory validator 306b may notify an operator with the shortlist of compounds and the particular property for laboratory experiments. The operator may send the shortlist of compounds and request a laboratory to perform experiments to determine whether each of the shortlist of compounds has or exhibits the particular property. After the experiments have concluded, the experimental results and/or further training data associated with the shortlist of compounds and whether each have or are associated with the particular property may be sent to the laboratory validator 306b.

The laboratory validator 306b may, on receiving experimental results or training data in relation to the shortlist of compounds and their association with the particular property, be configured to output a labelled training dataset $\{T_k\}_j^L$ based on the experimental results corresponding to the shortlist of compounds. The labelled training dataset $\{T_k\}_j^L$ may be used as further training data $\{T_k\}_j$ for use, as described herein, by ML technique in generating/updating the property model $M_j$. The selector $V_T$ may be used to select the labelled training dataset $\{T_k\}_j^L$ as the further training dataset $\{T_k\}_j$ for training the ML technique to generating/updating the property model $M_j$.

Although the selector $V_T$ is shown as a switching circuit, switching between computer analysis/simulator validator 306a and laboratory validator 306b, this is by way of example only and the invention is not so limited, it is to be appreciated that the skilled person may use any other method, technique, apparatus, or hardware/software for selecting between and/or directing/requesting the shortlist of compounds to be processed in relation to the particular property by computer analysis/simulator validator 306a and/or laboratory validator 306b.

The a retraining mechanism 302 may implement the retraining steps of training process 110 or 130, which may be further modified to train the RL technique to generate a selection and/or validation model that selects both a shortlist of compounds and a validation method for validating the selected shortlist of compounds. The validation selector 306 may implement the validation model generated by the RL technique, but may include several rules for rewarding or penalising the RL technique when it is retrained in retraining mechanism 302. For example, given the laboratory experimentation is costly and time consuming, the validation selector 306 may inhibit the selection of performing laboratory experimentation too early in the training process when generating the selection model for selecting the shortlist and validation method.

As an example, when the validation selector 306 selects to perform laboratory experiments whilst the number of iterations for retraining the selection/validation model is below a predetermined threshold, then a validation penalty 308a (e.g. $PN_{j+1}$) may be fed back to the retraining mechanism 302 in the next iteration (e.g. j=j+1) for retraining the selection/validation method based on the penalty. The validation selector 306 may temporarily inhibit selection of validation using laboratory validator 306b and, instead, select the validation method to perform computer analysis using the computer analysis validator 306a.

In another example, when the validation selector 306 selects to perform laboratory experiments whilst it is determined that the validation method to perform computer analysis would further improve the property model score, then a validation penalty 308a (e.g. $PN_{j+1}$) may be fed back in the next iteration (e.g. j=j+1) to the retraining mechanism 302 for retraining the selection/validation method based on the penalty. This is to encourage the selection/validation model to use computer analysis for validating the shortlist as much as possible and minimising the cost and expense of laboratory experimentation. The validation selector 306 may temporarily inhibit selection of validation using laboratory validator 306b and, instead, select the validation method to perform computer analysis using the computer analysis validator 306a.

In a further example, when validation selector 306 selects to perform laboratory experiments whilst the selected shortlist of compounds has substantially changed from a previously selected shortlist of compounds, then a validation penalty 308a (e.g. $PN_{j+1}$) may be fed back in the next iteration (e.g. j=j+1) to the retraining mechanism 302 for retraining the selection/validation method based on the penalty. This is to encourage the selection/validation model to use computer analysis for validating the shortlist when it changes between iterations as this indicates that computer analysis is still useful for validating the shortlist and further minimises the cost and expense of laboratory experimentation. The validation selector 306 may temporarily inhibit selection of validation using laboratory validator 306b and, instead, select the validation method to perform computer analysis using the computer analysis validator 306a.

In another example, the validation selector 306 may select perform computer analysis is selected whilst it is determined that computer analysis will yield an improvement in an property model score for the property model based on previous property model scores calculated from corresponding prediction result lists generated after each shortlist of compounds has been validated. A validation reward 308b (e.g. $RW_{j+1}$) may be fed back in the next iteration (e.g. j=j+1) to the retraining mechanism 302 for retraining the selection/validation method based on the reward. The validation selector 306 proceeds to allow the validation method to perform computer analysis using the computer analysis validator 306a.

In another example, the validation selector 306 may select to perform laboratory analysis whilst it is determined that computer analysis will not yield an improvement in an property model score for the property model based on previous property model scores calculated from corresponding prediction result lists generated after each shortlist of compounds has been validated; and it is determined that the shortlist of compounds is small enough for laboratory analysis. Then a validation reward 308b (e.g. $RW_{j+1}$) may be fed back in the next iteration (e.g. j=j+1) to the retraining mechanism 302 for retraining the selection/validation method based on the reward. The validation selector 306 proceeds to allow the validation method to perform laboratory analysis using the laboratory analysis validator 306b on the selected shortlist of compounds.

Although several examples of providing a penalty or reward, by way of example only but not limited to, a fed back signal representing a validation penalty 308a (e.g. $PN_{j+1}$) or validation reward 308b (e.g. $RW_{j+1}$) for retraining the selection model/validation model in the next iteration, it is to be appreciated by the skilled person that any other method/mechanism for retraining the selection/validation model may be used and that the penalty or reward may be provided by the validation selector 306 as a continuous or discrete value at any time to the retraining mechanism. For example, the retraining mechanism may perform mini-retraining loops iterations within each main iteration j. Each mini-retraining loop may include, by way of example only but not limited to, the retraining mechanism 302, shortlist selector 304 and validation selector 306, in which multiple mini-iterations, i, may be performed for each iteration j in which the validation selector 306 feeds back validation penalty 308a (e.g. $PN_i$) or validation reward 308b (e.g. $RW_i$) to retraining mechanism 302 for retraining the selection model/validation model to select the appropriate validation method prior to performing the next iteration j+1.

Additionally or alternatively, selecting a validation method (e.g. computer analysis validator 306a and/or laboratory analysis validator 306b) may be performed heuristically, for example, the validation selector 306 may select that computer analysis/simulation using computer analysis validator 306a is to be performed for validating the shortlist of compounds. Once the property model stops improving based on the computer analysis/simulation validation, then the validator selector 306 may select that laboratory experiments using the laboratory analysis validator 306a are performed on an appropriately selected shortlist of compounds for validation. The experimental results may be used to update the property model, in which computer analysis/simulation using computer analysis validator 306a may then be selected one again until the property model stops improving. This may be repeated until the performance of the property model plateaus or stops improving regardless of whether computer simulation and/or laboratory experimentation is selected. Alternatively or additionally, this may be repeated a predetermined multiple times and/or until a predetermined number of iterations of performing laboratory experiments have been performed, and/or a predetermined number of iterations of performing computer simulations has been performed, and/or a combination of both.

Such heuristic techniques may also be combined with a training methodology for training the selection model to select an appropriate validation method for validating the shortlist of compounds, The heuristic techniques may be used to reward and/or punish the selection model for selecting an inappropriate validation method, and so may be used to step in and ensure that the appropriate validation method is selected. For example, this may be used to stop the selection model from selecting the laboratory analysis validator 306b for performing laboratory experiments too early when computer analysis/simulation validation may still yield an improved property model, and/or when the selection model is still training to select an appropriate shortlist of compounds for validation.

Figure 4:
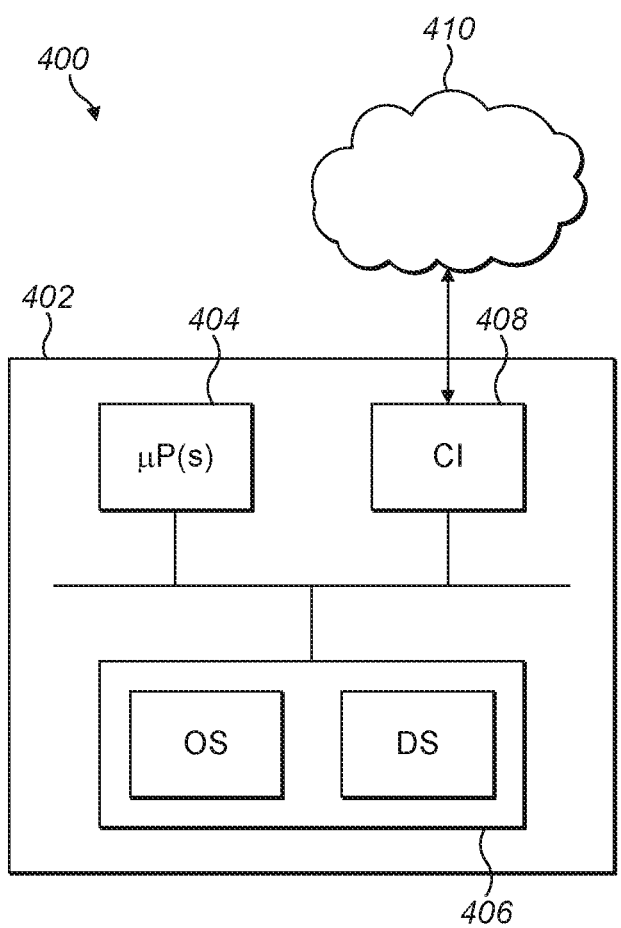
FIG. 4 is a schematic diagram of a computing device according to the invention.

FIG. 4 is a schematic diagram of a computing system 400 comprising a computing apparatus or device 402 according to the invention. The computing apparatus or device 402 may include a processor unit 404, a memory unit 406 and a communication interface 408. The processor unit 404 is connected to the memory unit 406 and the communication interface 408. The memory unit 406 may include an operating system (OS) and a data store (DS) that may include other applications and/or software such as, by way of example only but not limited to, computer-implemented method(s), process(as) and/or instruction code for implementing the method(s) and/or process(as) as described herein with reference to FIGS. 1a to 3. The processor unit 404 and memory unit 406 may be configured to implement one or more steps of one or more of the process(as) 110, 130 and/or as described with reference to FIGS. 1a to 3, and/or as described herein. The processor unit 404 may include one or more processor(s), controller(s) or any suitable type of hardware(s) for implementing computer executable instructions to control apparatus 402 according to the invention. The computing apparatus 402 may be connected via communication interface 408 to a network 412 for communicating and/or operating with other computing apparatus/system(s) (not shown) for implementing the invention accordingly.

The computing system 400 may be a server system, which may comprise a single server or network of servers configured to implement the invention as described herein. In some examples the functionality of the server may be provided by a network of servers distributed across a geographical area, such as a worldwide distributed network of servers, and a user may be connected to an appropriate one of the network of servers based upon a user location.

Further modifications or examples, may include a computer-implemented method for updating a property model, the property model for predicting whether a compound is associated with a particular property, in which the method includes the steps of: generating a result list of compounds using the property model on a plurality of compounds; selecting a shortlist of compounds from the plurality of compounds using a selection model according to any of the process(es) 110, 130 and/or apparatus/systems 100, 120, 300, and/or modifications thereof, and/or as herein described; receiving validation results (e.g. from computer analysis, laboratory experimentation, or labelled training datasets) for the shortlist of compounds; and updating the property model based on the validation results. These steps may be repeated until the property model is determined to be validly trained.

The method may include validating the association each of the shortlist of compounds has with the particular property, where validating outputs validation results comprising data representative of further labelled training data corresponding to the validated property associations of each compound in the shortlist of compounds. The property model may also be updated based on training a ML technique based on a labelled training dataset corresponding to multiple compounds and their association with a particular property.

An apparatus or computing device 402 including a processor 404, a memory unit 406 and a communication interface 408, where the processor 404 is connected to the memory unit 406 and the communication interface 408, where the processor 404, communication interface 408 and/or memory unit 406 are configured to implement the computer-implemented method for updating the property model.

Other modifications or examples may include a system for generating a selection model based on an ML technique (e.g. an RL technique or any other ML technique), the selection model is configured to select a shortlist of compounds for validation with a particular property. The system may include: a selection module or apparatus configured according to any of the process(es) 110, 130 and/or apparatus/systems 100, 120, 300, and/or modifications thereof, and/or as herein described, for selecting a shortlist of compounds; and a ML/property updating module or apparatus configured according to the computer-implemented method for updating the property model and/or the apparatus thereto, modifications thereof, and/or as herein described, where the property updating module or apparatus is coupled to the selection module, the property updating module or apparatus being configured to update the property model based on the selected shortlist of compounds.

In yet further modifications, a system may be provided that includes: a property model generation module configured for generating a property model based on a labelled training dataset, the labelled training dataset comprising data representative of compounds associated with a particular property; an ML test module configured for generating a prediction result list output from the generated property model for predicting whether a plurality of compounds are associated with a particular property and a property model score associated with the predictions; and a selection module configured according to any one of the process(es) 110, 130 and/or apparatus/systems 100, 120, 300, and/or modifications thereof, and/or as herein described, for selecting a shortlist of compounds from the prediction result list for validation, where validating the shortlist of compounds outputs validation results for updating the property model. The property model generation module may be further configured to receive a further labelled training dataset based on the validation results of the shortlist of compounds, and update the property model by generating a property model based on the labelled training dataset and the further labelled training dataset. The system may include one or more further modifications, features, steps and/or features of the process(es) 110, 130 and/or apparatus/systems 100, 120, 300, and/or modifications thereof, and/or as herein described.

Furthermore, the apparatus and/or system(s) 100, 120, 300, process(es) 110 and/or 130, and/or the method(s)/process(es) as described with reference to one or more of FIGS. 1*a*-4 may be implemented in hardware and/or software. For example, the method(s) and/or process(es) for training and/or implementing a selection model and/or for using a selection model described with reference to one or more of FIGS. 1*a*-4 may be implemented in hardware and/or software such as, by way of example only but not limited to, as a computer-implemented method by one or more processor(s)/processor unit(s) or as the application demands. Such apparatus, system(s), process(es) and/or method(s) may be used to generate an ML model comprising data representative of a selection model generated as described with respect to apparatus and/or system(s) 100, 120, 300, process(es) 110 and/or 130, and/or the apparatus, systems and/or method(s)/process(es) as described with reference to one or more of FIGS. 1*a*-4, modifications thereof and/or as described herein and the like. Thus, a ML selection model may be obtained from apparatus, systems and/or computer-implemented process(es), method(s) as described herein. Furthermore, a ML validation model may also be obtained from the apparatus and/or system(s) 100, 120, 300, process(es) 110 and/or 130, and/or the apparatus, systems and/or method(s)/process(es) as described with reference to one or more of FIGS. 1*a*-4, some of which may be implemented in hardware and/or software such as, by way of example only but not limited to, a computer-implemented method that may be executed on a processor or processor unit or as the application demands, as described with reference to one or more of FIGS. 1*a*-4, modifications thereof, and/or as described herein and the like.

The above description discusses embodiments of the invention with reference to a single user for clarity. It will be understood that in practice the system may be shared by a plurality of users, and possibly by a very large number of users simultaneously.

The embodiments described above are fully automatic. In some examples a user or operator of the system may manually instruct some steps of the method to be carried out.

In the described embodiments of the invention the system may be implemented as any form of a computing and/or electronic device. Such a device may comprise one or more processors which may be microprocessors, controllers or any other suitable type of processors for processing computer executable instructions to control the operation of the device in order to gather and record routing information. In some examples, for example where a system on a chip architecture is used, the processors may include one or more fixed function blocks (also referred to as accelerators) which implement a part of the method in hardware (rather than software or firmware). Platform software comprising an operating system or any other suitable platform software may be provided at the computing-based device to enable application software to be executed on the device.

Various functions described herein can be implemented in hardware, software, or any combination thereof. If implemented in software, the functions can be stored on or transmitted over as one or more instructions or code on a computer-readable medium. Computer-readable media may include, for example, computer-readable storage media. Computer-readable storage media may include volatile or non-volatile, removable or non-removable media implemented in any method or technology for storage of information such as computer readable instructions, data structures, program modules or other data. A computer-readable storage media can be any available storage media that may be accessed by a computer. By way of example, and not limitation, such computer-readable storage media may comprise RAM, ROM, EEPROM, flash memory or other memory devices, CD-ROM or other optical disc storage, magnetic disc storage or other magnetic storage devices, or any other medium that can be used to carry or store desired program code in the form of instructions or data structures and that can be accessed by a computer. Disc and disk, as used herein, include compact disc (CD), laser disc, optical disc, digital versatile disc (DVD), floppy disk, and blu-ray disc (BD). Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, DSL, or wireless technologies such as infrared, radio, and microwave are included in the definition of communication medium. Combinations of the above should also be included within the scope of computer-readable media.

Alternatively, or in addition, the functionality described herein can be performed, at least in part, by one or more hardware logic components. For example, and without limitation, hardware logic components that can be used may include Field-programmable Gate Arrays (FPGAs), Program-specific Integrated Circuits (ASICs), Program-specific Standard Products (ASSPs), System-on-a-chip systems (SOCs). Complex Programmable Logic Devices (CPLDs), etc.

Although illustrated as a single system, it is to be understood that the computing device may be a distributed system. Thus, for instance, several devices may be in communication by way of a network connection and may collectively perform tasks described as being performed by the computing device.

Although illustrated as a local device it will be appreciated that the computing device may be located remotely and accessed via a network or other communication link (for example using a communication interface).

The term 'computer' is used herein to refer to any device with processing capability such that it can execute instructions. Those skilled in the art will realise that such processing capabilities are incorporated into many different devices and therefore the term 'computer' includes PCs, servers, mobile telephones, personal digital assistants and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

It will be understood that the benefits and advantages described above may relate to one embodiment or may relate to several embodiments. The embodiments are not limited to those that solve any or all of the stated problems or those that have any or all of the stated benefits and advantages. Variants should be considered to be included into the scope of the invention.

Any reference to 'an' item refers to one or more of those items. The term 'comprising' is used herein to mean including the method steps or elements identified, but that such steps or elements do not comprise an exclusive list and a method or apparatus may contain additional steps or elements.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something".

Further, to the extent that the term "includes" is used in either the detailed description or the claims, such term is intended to be inclusive in a manner similar to the term "comprising" as "comprising" is interpreted when employed as a transitional word in a claim.

The figures illustrate exemplary methods. While the methods are shown and described as being a series of acts that are performed in a particular sequence, it is to be understood and appreciated that the methods are not limited by the order of the sequence. For example, some acts can occur in a different order than what is described herein. In addition, an act can occur concurrently with another act. Further, in some instances, not all acts may be required to implement a method described herein.

Moreover, the acts described herein may comprise computer-executable instructions that can be implemented by one or more processors and/or stored on a computer-readable medium or media. The computer-executable instructions can include routines, sub-routines, programs, threads of execution, and/or the like. Still further, results of acts of the methods can be stored in a computer-readable medium, displayed on a display device, and/or the like.

The order of the steps of the methods described herein is exemplary, but the steps may be carried out in any suitable order, or simultaneously where appropriate. Additionally, steps may be added or substituted in, or individual steps may be deleted from any of the methods without departing from the scope of the subject matter described herein. Aspects of any of the examples described above may be combined with aspects of any of the other examples described to form further examples without losing the effect sought.

It will be understood that the above description of a preferred embodiment is given by way of example only and that various modifications may be made by those skilled in the art. What has been described above includes examples of one or more embodiments. It is, of course, not possible to describe every conceivable modification and alteration of the above devices or methods for purposes of describing the aforementioned aspects, but one of ordinary skill in the art can recognize that many further modifications and permutations of various aspects are possible. Accordingly, the described aspects are intended to embrace all such alterations, modifications, and variations that fall within the scope of the appended claims.

The invention claimed is:

1. A computer-implemented method of generating an artificial intelligence selection model which selects a shortlist of compounds for validation in relation to a particular property, the method comprising:
   receiving a prediction result list output from an artificial intelligence property model which predicts whether each of a plurality of compounds has the particular property and calculating a property model score based on the prediction result list, wherein the property model score estimates the quality of the property model;
   generating the selection model by training a machine learning (ML) technique based on the property model score, wherein the ML technique comprises an artificial neural network;
   using the trained selection model, selecting from the prediction result list a shortlist of compounds for validation from the plurality of compounds;
   sending the selected shortlist of compounds for validation with the particular property;

validating whether each of the compounds in the selected shortlist of compounds has the particular property;

updating the property model based on the validation; and repeating at least the receiving of the prediction result list from the property model and training of the selection model until it is determined that the selection model has been validly trained, wherein the selection model is determined to be validly trained when (a) there are no more compounds that need to be selected for the shortlist of compounds, (b) the property model score indicates that the performance of the ML technique has plateaued, or (c) there are no more compounds that need to be selected for the shortlist of compounds and the property model score indicates that the performance of the ML technique has plateaued.

2. The computer-implemented method according to claim 1, wherein training the selection model further comprises determining whether to train the selection model for selecting a shortlist of compounds based on the property model score and one or more previous property model scores.

3. The computer-implemented method as claimed in claim 1, wherein the property model is trained using a labelled training dataset, the labelled training dataset being associated with at least a subset of the plurality of compounds in relation to the particular property, and wherein the validation shortlist of compounds are incorporated into the labelled training dataset for updating the property model.

4. The computer-implemented method as claimed in claim 1, wherein validating the shortlist of compounds further comprises validating that each compound from the shortlist of compounds has the particular property based on either laboratory experimentation or computer analysis.

5. The computer-implemented method as claimed in claim 4, wherein:
the laboratory experimentation outputs a set of laboratory experimental validation results in relation to the shortlist of compounds and the property, wherein the property model is updated based on the laboratory experimentation validation results and the ML technique used to generate the property model; or
the computer analysis outputs a set of computer analysis validation results in relation to the selected shortlist of compounds and the particular property, wherein the property model is updated based on the computer analysis validation results and the ML technique used to generate the property model.

6. A computer-implemented method as claimed in claim 1, wherein:
the selection model is further trained to select a validation method for validating the selected shortlist of compounds;
selecting the validation method for validating the selected shortlist of compounds further comprises selecting whether to perform laboratory experimentation or to perform computer analysis based on the particular property and the selected shortlist of compounds;
the laboratory experimentation outputs laboratory experimentation validation results for estimating whether each compound on the selected shortlist of compounds has the particular property, the laboratory experimental validation results being used for updating the property model; and
the computer analysis outputs computer analysis validation results for estimating whether each compound on the selected shortlist of compounds has the particular property, the computer analysis validation results being used for updating the property model.

7. The computer-implemented method as claimed in claim 5, the method further comprising:
receiving the prediction result list output from the property model for predicting whether a plurality of compounds have a particular property and a property model score;
determining whether to train the selection model for selecting a shortlist of compounds and a validation method based on the property model score and one or more previous property model scores; and
training the selection model based on the property model score, the prediction result list, or the property model score and the prediction result list.

8. The computer-implemented method according to claim 6, wherein when the validation method to perform laboratory experimentation is selected and the number of iterations for training the selection model is below a predetermined threshold, the method further comprising:
penalising the selection model during retraining; and
performing the computer analysis.

9. The computer-implemented method according to claim 6, wherein when the validation method to perform laboratory experiments is selected and it is determined that the validation method to perform computer analysis would further improve the property model score, the method further comprising:
penalising the selection model during retraining; and
performing the computer analysis.

10. The computer-implemented method according to claim 6, wherein when the validation method to perform laboratory experiments is selected and the selected shortlist of compounds has substantially changed from a previously selected shortlist of compounds, the method further comprising:
penalising the selection model during retraining; and
performing the computer analysis.

11. The computer-implemented method according to claim 6, wherein when the computer analysis is selected as the validation method and it is determined that the computer analysis will yield an improvement in the property model score for the property model based on previous property model scores calculated from corresponding prediction result lists generated after each shortlist of compounds has been validated, the method further comprising:
rewarding the selection model during retraining; and
performing the computer analysis.

12. The computer-implemented method according to claim 1, wherein the prediction result list comprises, for each compound listed, a prediction property score indicating whether said compound has the particular property.

13. The computer-implemented method according to claim 12, wherein the prediction property score comprises a certainty score, wherein compounds that are known to have the particular property are given a positive certainty score, compounds that are known not to have the particular property are given a negative certainty score, and other compounds are given an uncertainty score between the positive certainty score and the negative certainty score.

14. The computer-implemented method according to claim 13, wherein the certainty score is a percentage certainty score, wherein the positive certainty score is 100%, the negative certainty score is 0%, and the uncertainty score is between 0% and 100%.

15. The computer-implemented method according to claim 1, wherein training the selection model further comprises:

indicating to a ML technique associated with the property model to revert the property model to a previous state when the property model score does not reach a property model performance threshold compared with the corresponding previous property model score;

indicating to the ML technique associated with the property model to retain the updated property model over a previous property model when the property model score is indicative of meeting or exceeding the property model performance threshold compared with the corresponding previous property model score;

training the selection model to select a set of compounds from the corresponding prediction result list based on the property model score; and repeating the steps of claim 1 until the selection model is determined to be validly trained.

16. A computer-implemented method of claim 15, wherein determining whether the selection model is validly trained further comprises:

comparing the retained property model score with one or more previous retained property model scores; and determining the selection model has been validly trained based on a plateau of property model scores.

17. The computer-implemented method according to claim 1, wherein the ML technique for generating the selection model comprises at least one of:

a recurrent neural network;
convolutional neural network;
reinforcement learning algorithm; or
any neural network structure.

18. The computer-implemented method according to claim 1, wherein the particular property includes a property or characteristic indicative of:

a compound docking with another compound to form a stable complex;

a ligand docking with a target protein, wherein the compound is the ligand;

a compound docking or binding with one or more target proteins;

a compound having a particular solubility or range of solubilities;

a compound having a particular toxicity;

any other property or characteristic associated with a compound that can be simulated based on computer simulation(s) and physical movements of atoms and molecules;

any other property or characteristic associated with a compound that can be determined from an expert knowledgebase; and any other property or characteristic associated with a compound that can be determined from an experimentation.

19. The computer-implemented method according to claim 1, wherein the ML technique for generating the selection model is different to the ML technique for generating or updating the property model.

20. The computer-implemented method according to claim 1, wherein the step of training the selection model further comprises training the selection model based on the property model score and the prediction result list.

21. The computer-implemented method according to claim 1, wherein training the selection model based on the prediction result list further comprises training the selection model based on one or more discrepancies between validation results associated with the validation of the shortlist of compounds and the current prediction result list or one or more previous prediction result lists output from the property model in its current state or one or more prior states.

22. The computer-implemented method according to claim 20, wherein using the prediction result list to train the selection model comprises training the selection model based on structures of compounds the property model is likely to incorrectly predict.

23. An apparatus comprising a processor, a memory unit, computer executable instructions, and a communication interface, wherein the processor is connected to the memory unit and the communication interface, wherein the computer executable instructions, when executed by the processor, cause the apparatus to:

receive a prediction result list output from an artificial intelligence property model which predicts whether each of a plurality of compounds has a particular property and calculate a property model score based on the prediction result list, wherein the property model score estimates the quality of the property model;

generate an artificial intelligence selection model which selects a shortlist of compounds for validation in relation to a particular property by training a machine learning (ML) technique based on the property model score, wherein the ML technique comprises an artificial neural network;

using the trained selection model, select from the prediction result list a shortlist of compounds for validation from the plurality of compounds;

send the shortlist of compounds for validation with the particular property;

validate whether each of the compounds in the shortlist of compounds has the particular property;

update the property model based on the validation; and repeat at least the receiving of the prediction result list from the property model and training of the selection model until it is determined that the selection model has been validly trained, wherein the selection model is determined to be validly trained when (a) there are no more compounds that need to be selected for the shortlist of compounds, (b) the property model score indicates that the performance of the ML technique has plateaued, or (c) there are no more compounds that need to be selected for the shortlist of compounds and the property model score indicates that the performance of the ML technique has plateaued.

24. A non-transitory tangible computer-readable storage medium on which are stored computer executable instructions that when executed by a computer causes the processor to effect a method comprising:

receiving a prediction result list output from an artificial intelligence property model which predicts whether each of a plurality of compounds has a particular property and calculating a property model score based on the prediction result list, wherein the property model score estimates the quality of the property model;

generating an artificial intelligence selection model by training a machine learning (ML) technique based on the property model score, wherein the ML technique comprises an artificial neural network;

using the trained selection model, selecting from the prediction result list a shortlist of compounds for validation from the plurality of compounds;

sending the selected shortlist of compounds for validation with the particular property;

validating whether each of the compounds in the selected shortlist of compounds has the particular property;

updating the property model based on the validation; and repeating at least the receiving of the prediction result list from the property model and training of the selection model until it is determined that the selection model has been validly trained, wherein the selection model is determined to be validly trained when (a) there are no more compounds that need to be selected for the shortlist of compounds, (b) the property model score indicates that the performance of the ML technique has plateaued, or (c) there are no more compounds that need to be selected for the shortlist of compounds and the property model score indicates that the performance of the ML technique has plateaued.

25. An apparatus for generating an artificial intelligence selection model based on a machine learning (ML) technique, the selection model configured to select a shortlist of compounds for validation with a particular property, the apparatus configured to:
receive a prediction result list output from an artificial intelligence property model which predicts whether each of a plurality of compounds has a particular property and calculate a property model score based on the prediction result list, wherein the property model score estimates the quality of the property model;
generate an artificial intelligence selection model which selects a shortlist of compounds for validation in relation to a particular property by training a machine learning (ML) technique based on the property model score, wherein the ML technique comprises an artificial neural network;
using the trained selection model, select from the prediction result list a shortlist of compounds for validation from the plurality of compounds;
send the selected shortlist of compounds for validation with the particular property;
validate whether each of the compounds in the selected shortlist of compounds has the particular property;
update the property model based on the validation; and
repeat at least the receiving of the prediction result list from the property model and training of the selection model until it is determined that the selection model has been validly trained, wherein the selection model is determined to be validly trained when (a) there are no more compounds that need to be selected for the shortlist of compounds, (b) the property model score indicates that the performance of the ML technique has plateaued, or (c) there are no more compounds that need to be selected for the shortlist of compounds and the property model score indicates that the performance of the ML technique has plateaued.

26. A computer-implemented method for updating an artificial intelligence property model, the property model configured to predict whether a compound is associated with a particular property, the method comprising:
processing information on a plurality of compounds using the property model and generating a result list of compounds;
selecting a shortlist of compounds from the plurality of compounds using an artificial intelligence selection model according to claim 1;
receiving validation results for the shortlist of compounds; and
updating the property model based on the validation results.

27. The computer-implemented method of claim 26, further comprising repeating the steps of processing and generating, selecting, and receiving until the property model is determined to be validly trained.

28. The computer-implemented method of claim 26, further comprising validating an association each of the shortlist of compounds has with the particular property, wherein validating outputs validation results comprising data representative of further labelled training data corresponding to the validated property association of each compound in the shortlist of compounds.

29. The computer-implemented method of claim 26, wherein the property model is updated based on training a machine learning technique based on a labelled training dataset corresponding to multiple compounds and their association with the particular property, the machine learning technique comprising an artificial neural network.

30. An apparatus comprising a processor, a memory unit, computer executable instructions, and a communication interface, wherein the processor is connected to the memory unit and the communication interface, and wherein, the computer executable instructions, when executed by the processor, cause the apparatus to update an artificial intelligence property model configured to predict whether a compound is associated with a particular property by:
processing information on a plurality of compounds using the property model and generating a result list of compounds;
selecting a shortlist of compounds from the plurality of compounds using an artificial intelligence selection model according to claim 1;
receiving validation results for the shortlist of compounds; and
updating the property model based on the validation results.

* * * * *